(12) United States Patent
Horlick et al.

(10) Patent No.: US 7,041,463 B2
(45) Date of Patent: May 9, 2006

(54) ORTHOLOGUES OF HUMAN RECEPTORS AND METHODS OF USE

(75) Inventors: Robert Horlick, San Diego, CA (US); Jiuquao Zhao, Hockessin (DE); Robert Swanson, Cranbury, NJ (US); Maria Webb, Flemington, NJ (US); Barbara Strohl, Hamilton, NJ (US); John J. Baldwin, Gwynedd Valley, PA (US); Douglas S. Auld, Cranbury, NJ (US); Xiao Ge Chen, Princton, NJ (US)

(73) Assignee: Pharmacopeia Drug Discovery, Inc., Cranbury, NJ (US)

( * ) Notice: Subject to any disclaimer, the term of this patent is extended or adjusted under 35 U.S.C. 154(b) by 484 days.

(21) Appl. No.: 10/237,563

(22) Filed: Sep. 9, 2002

(65) Prior Publication Data

US 2003/0082660 A1    May 1, 2003

Related U.S. Application Data

(63) Continuation-in-part of application No. 09/576,160, filed on May 22, 2000, now Pat. No. 6,469,150.

(51) Int. Cl.
*G01N 33/567*    (2006.01)

(52) U.S. Cl. .................. 435/7.21; 435/7.1; 435/7.2

(58) Field of Classification Search ............... None
See application file for complete search history.

(56) References Cited

U.S. PATENT DOCUMENTS

| | | | | |
|---|---|---|---|---|
| 5,712,111 | A | * | 1/1998 | Linemeyer et al. ......... 435/69.1 |
| 5,783,415 | A | | 7/1998 | Lee et al. ................. 435/69.1 |
| 5,856,457 | A | | 1/1999 | Lee et al. ................. 536/23.5 |
| 5,965,367 | A | | 10/1999 | Linemeyer et al. ............ 435/6 |
| 6,469,150 | B1 | | 10/2002 | Horlick et al. ............. 536/23.1 |

OTHER PUBLICATIONS

Calixto et al. 2000. Pain 87:1-5.*
Judith M. Hall, "Bradykinin Receptors," Gen. Pharmac., 28 (1) 1-6 (1997).
Jones et al., "Molecular characterisation of cloned bradykinin B1 receptors from rat and human," European Journal of Pharmacology, 374 423-433 (1999).
Ni et al., "Molecular cloning and expression of rat bradykinin B1 receptor," Biochimica et Biophysica Acta 1442 177-185 (1998).
Pesquero et al., "Molecular Cloning and Functional Charaterization of a Mouse Bradykinin B1 Receptor Gene," Biomedical and Biophysical Research Communications 220 219-225 (1996).
Menke et al., "Expression Cloning of a Human B1 Bradykinin Receptor," J. Biol. Chem., 269, (34) 21583-21586 (1994).
GenBank Accession No. AJ132230, (1999).

GenBank Accession No. X69681, (1993).
MacNeil et al., "Cloning and pharmacological characterization of a rabbit bradykinin B1 receptor," Biochimica et Biophysica Acta 1264 223-228 (1995).
GenBank Accession No. U47281, (1996).
GenBank Accession No. U44436.
Genbank Accession No. L42383, (1996).
GenBank Accession No. U12512, (1994).
GenBank Accession No. NM_000710, (1994).
Tian et al., "A Small, nonpeptidyl Mimic of Granulocyte-Colony-Stimulating Factor," Science, 281, 257-259 (1998).
Alvarez et al., "Charaterization of interleukin-8 receptors in non-human primates," Immunogenetics 43: (5) 261-267 (1996).
GenBank Accession No. CAA62565, (1996).
GenBank Accession No. CAA62563, (1996).
GenBank Accession No. X91113, (1996).
Ji et al., "Genetic transfer of a nonpeptide antagonist binding site to a previously unresponsive angiotensin receptor," Proc. Natl. Acad. Sci. USA, 92, 9240-9244 (1995).
Gether et al., "Different binding epitopes on the NK1 receptor for substance P and a non-peptide antagonist," Nature, 362, 345-348 (1993).
Sachnis et al., "Molecular Basis for the Species Selectively of the Substance P Antagonist CP-96,345," The Jounral of Biological Chemistry, 268: (4) 2319-2323 (1993).
Fong et al., "Molecular Basis for the Species Selectively of the Neurokinin-1 Receptor Antagonists CP-96,345 and RP67580," J. Biol. Chem., 267: (36) pp. 25668-25671 (1992).
Beinborn et al., "A single amino acid of the cholecystokinin-B/gastrin receptor determines specificity for non-peptide antagonists," Nature, 362, pp. 348-350 (1993).
Oksenberg et al., "A single amino-acid difference confers major pharmacological variation between human and rodent 5-HT 1B receptors," Nature 360 pp. 161-163 (1992).

* cited by examiner

*Primary Examiner*—Anthony C. Caputa
*Assistant Examiner*—Daniel E. Kolker
(74) *Attorney, Agent, or Firm*—Heslin Rothenberg Farley Mesiti P.C.; Kathy Smith Dias

(57) ABSTRACT

Methods for identifying modulators of receptor activity using orthologues of human receptors are described. Additionally, a method for identifying an animal model useful in the screening of potential therapeutic agents is provided. The genes for bradykinin $B_1$ receptors from five mammalian species, vervet monkey, rhesus macaque, tree shrew, dog and pig, as well as the genes for CXCR2 receptors from chimpanzee, gorilla, orangutan, rhesus, vervet and baboon have been cloned and characterized and are described herein.

5 Claims, 19 Drawing Sheets

Figure 3. Pair Distances of B1 Protein Sequences from nine species

| Human | Vervet | Rhesus | Tree Shrew | Dog | Rabbit | Pig | Mouse | Rat | |
|---|---|---|---|---|---|---|---|---|---|
| *** | 96 | 96.3 | 80.5 | 75.3 | 77.1 | 72.3 | 71 | 68.6 | Human |
| | *** | 97.7 | 80.5 | 75 | 77.3 | 73.1 | 71.3 | 68.6 | Vervet |
| | | *** | 81.6 | 75 | 77.3 | 73.1 | 70.7 | 68.3 | Rhesus |
| | | | *** | 71.9 | 75.9 | 70.3 | 70.4 | 68.6 | Tree Shrew |
| | | | | *** | 71.9 | 69.4 | 67.8 | 66.9 | Dog |
| | | | | | *** | 72.2 | 72.2 | 67.8 | Rabbit |
| | | | | | | *** | 67.2 | 64.5 | Pig |
| | | | | | | | *** | 88.1 | Mouse |
| | | | | | | | | *** | Rat |

Dog sequence is from amino acid 1-320 only. Numbers represent percent identity.

FIGURE 3

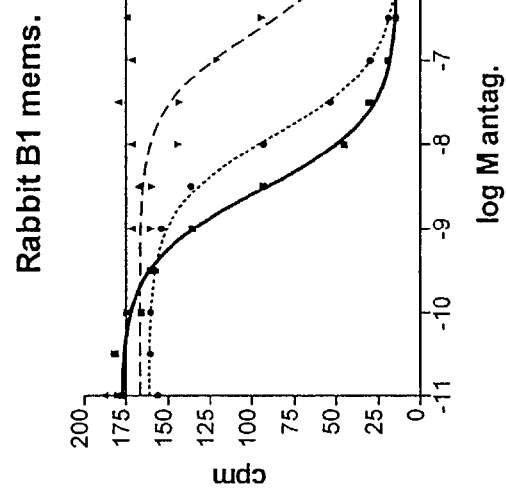
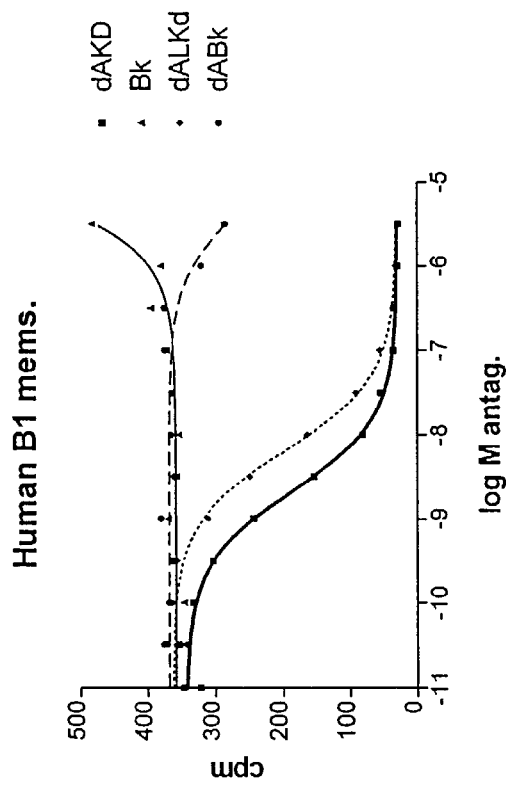
FIGURE 7

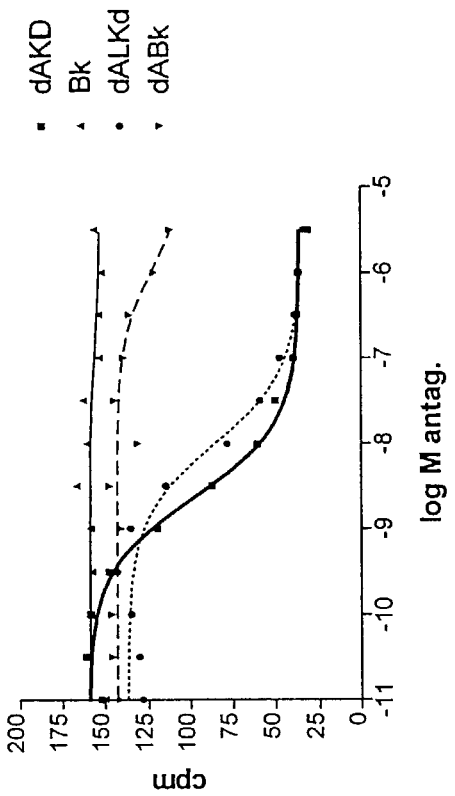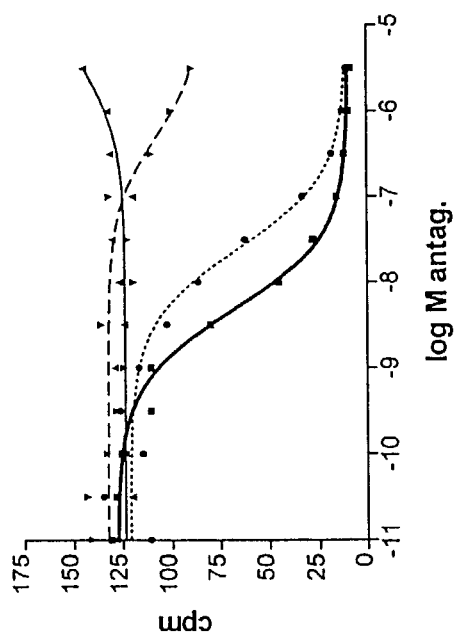
FIGURE 8

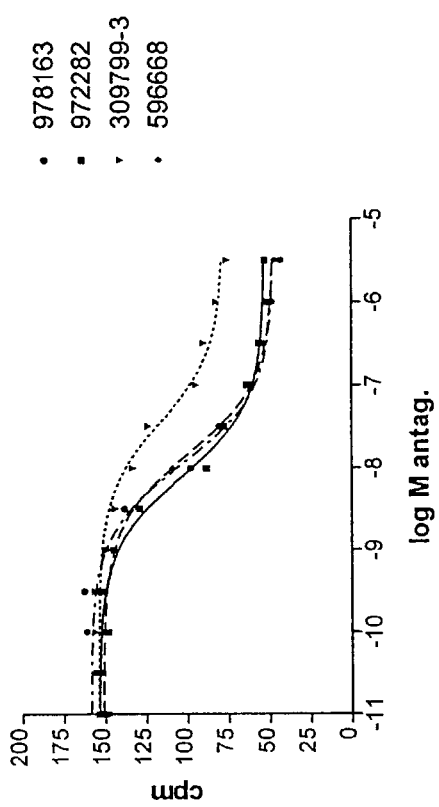
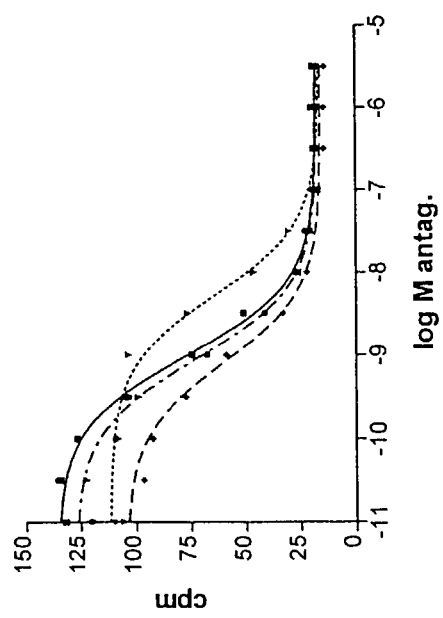
FIGURE 11

FIGURE 13

Average Kd values for dALKd

| orthologue | Avg Kd ± SEM | n= |
|---|---|---|
| hB1 | 0.6 ± 0.1 | 7 |
| mB1 | 2.8 ± 1.0 | 5 |
| LB1 | 1.3 ± 0.1 | 3 |
| tB1 | 4.2 ± 1.0 | 2 |
| pB1 | 1.9 ± 0.7 | 3 |
| dB1 | 3.3 ± 0.2 | 2 |

Average Ki values in nM

| | Human | Rabbit | ree Shre | Rhesus | Pig | Dog |
|---|---|---|---|---|---|---|
| dAKd | 1.5 ± 0.7 | 3.4 ± 1.0 | 6.1 ± 1.2 | 3.3 ± 2.4 | 2.3 ± 1.0 | 4.2 ± 1.2 |
| BK | IA | IA | IA | IA | IA | IA |
| dALKd | 4.6 ± 2.1 | 9.3 ± 1.5 | 22 ± 6 | 9.5 ± 5.3 | 9.5 ± 2.7 | 120 ± 36 |
| dABK | IA | 248 ± 139 | IA | 22.8 ± 4.6 | 218 ± 94 | 7.6 ± 1.2 |
| PS309799 | 17.3 ± 1.5 | IA | 3.3 ± 0.9 | 13.0 ± 5.1 | IA | IA |
| PS596668 | 5.7 ± 1.5 | 27.7 ± 6.4 | 0.6 ± 0.2 | 7.5 ± 1.1 | 33.3 ± 8.9 | IA |
| PS972282 | 6.3 ± 0.4 | 15.1 ± 8.4 | 0.9 ± 0.1 | 10.3 ± 5.6 | 22.5 ± 8.1 | 50.3 ± 6.7 |
| PS978163 | 6.3 ± 1.1 | 20.8 ± 5.9 | 0.9 ± 0.2 | 10.3 ± 5.6 | 63.7 ± 24.6 | 363 ± 57 |

309799  tree shrew > human > Rhesus macaque >> pig > dog, rabbit
596668  tree shrew > human > Rhesus macaque > rabbit > pig >> dog
972282  tree shrew > human = Rhesus macaque > rabbit > pig > dog
978163  tree shrew > human > Rhesus macaque > rabbit > pig > dog

Phylogenetics Tree based on primate IL8RB DNA sequences

DNA sequence relatedness of various primate IL8RB

| Percent Similarity in upper triangle | Human | Chimp | Chimp | Gorilla | Gorilla | Orangutan | Orangutan | Rhesus | Rhesus | Vervet | Baboon |
|---|---|---|---|---|---|---|---|---|---|---|---|
| Human (M94582) | *** | 99.4 | 99.3 | 98.7 | 98.2 | 97.6 | 97.8 | 94 | 98.6 | 93.4 | 93.5 |
| Chimpanzee PCOP | 0.6 | *** | 99.3 | 98.5 | 98 | 97.2 | 97.3 | 93.8 | 98 | 93.2 | 93.4 |
| Chimpanzee (X91113) | 0.7 | 0.7 | *** | 98.2 | 97.9 | 96.9 | 97.3 | 93.7 | 98.1 | 93.2 | 93.4 |
| Gorilla PCOP | 1.2 | 1.4 | 1.7 | *** | 99.5 | 97.7 | 97.5 | 93.8 | 97.7 | 93.6 | 93.4 |
| Gorilla (X91114) | 1.7 | 1.9 | 2 | 0.5 | *** | 97.2 | 97.4 | 93.5 | 97.2 | 93.2 | 93.4 |
| Orangutan PCOP | 2.4 | 2.8 | 3.1 | 2.3 | 2.8 | *** | 97.2 | 93.7 | 96.7 | 93.1 | 93.4 |
| Orangutan (X91115) | 2.1 | 2.7 | 2.6 | 2.4 | 2.5 | 2.5 | *** | 93.5 | 96.4 | 92.6 | 93.3 |
| Rhesus PCOP | 5.9 | 6.1 | 6.4 | 6 | 6.3 | 6.2 | 6.5 | *** | 94.9 | 97.2 | 97.7 |
| Rhesus (X91116) | 1.3 | 1.9 | 1.9 | 2.2 | 2.7 | 3.2 | 3.5 | 5.1 | *** | 94.3 | 94.2 |
| Vervet PCOP | 6.3 | 6.5 | 6.7 | 6.1 | 6.6 | 6.7 | 7.2 | 2.9 | 5.5 | *** | 96.4 |
| Baboon PCOP | 6 | 6.2 | 6.3 | 6.1 | 6.2 | 6.1 | 6.4 | 2.3 | 5.4 | 3.5 | *** |
| Percent Divergence in lower triangle | | | | | | | | | | | |

FIGURE 16

Protein sequence relatedness of various primate IL8RB

| Percent Similarity in upper triangle | Human | Chimp | Chimp | Gorilla | Gorilla | Orangutan | Orangutan | Rhesus | Rhesus | Vervet | Baboon |
|---|---|---|---|---|---|---|---|---|---|---|---|
| Human (M94582) | *** | 99.7 | 99.2 | 98 | 97.2 | 95.5 | 95.5 | 90.4 | 97.5 | 89.6 | 89.9 |
| Chimpanzee PCOP | 0 | *** | 99.2 | 98 | 97.2 | 95.5 | 95.5 | 90.4 | 97.5 | 89.6 | 89.9 |
| Chimpanzee (X91113) | 0.6 | 0.6 | *** | 97.5 | 97.2 | 94.9 | 95.5 | 89.9 | 96.9 | 89 | 89.9 |
| Gorilla PCOP | 1.7 | 1.7 | 2.3 | *** | 98.6 | 96.1 | 95.5 | 90.2 | 96.3 | 89.9 | 89.9 |
| Gorilla (X91114) | 2.6 | 2.6 | 2.6 | 1.1 | *** | 94.9 | 95.8 | 89.6 | 95.2 | 88.8 | 89.9 |
| Orangutan PCOP | 4.4 | 4.4 | 5 | 3.8 | 5 | *** | 95.8 | 89.6 | 94.4 | 89.3 | 89.9 |
| Orangutan (X91115) | 4.4 | 4.4 | 4.4 | 4.4 | 4.1 | 4.1 | *** | 89 | 93.3 | 87.6 | 89.6 |
| Rhesus PCOP | 9.9 | 9.9 | 10.6 | 10.3 | 10.9 | 10.9 | 11.6 | *** | 92.4 | 95.5 | 95.5 |
| Rhesus (X91116) | 2.3 | 2.3 | 2.9 | 3.5 | 4.7 | 5.6 | 6.8 | 7.7 | *** | 91.6 | 91.3 |
| Vervet PCOP | 10.9 | 10.9 | 11.6 | 10.6 | 11.9 | 11.2 | 13.2 | 4.4 | 8.7 | *** | 93.5 |
| Baboon PCOP | 10.6 | 10.6 | 10.6 | 10.6 | 10.6 | 10.6 | 10.9 | 4.4 | 9 | 6.5 | *** |
| Percent Divergence in lower triangle | | | | | | | | | | | |

FIGURE 17

Example displacement-binding data

Figure 18. A compound with selectivity for various species

Example displacement-binding data (continued)

Figure 19. A non-selective compound

SEQUENCE LISTING

<160> NUMBER OF SEQ ID NOS: 63

<210> SEQ ID NO 1
<211> LENGTH: 352
<212> TYPE: PRT
<213> ORGANISM: Cercopithecus pygerythrus

<400> SEQUENCE: 1

Met Ala Ser Trp Pro Pro Leu Glu Leu Gln Ser Ser Asn Gln Ser Gln

```
              1               5              10              15
            Leu Phe Pro Gln Asn Ala Thr Ala Cys Asp Asn Ala Pro Glu Ala Trp
                         20                  25                  30

Asp Leu Leu His Arg Val Leu Pro Thr Phe Ile Ile Ser Ile Cys Ser
                         35                  40                  45

Phe Gly Leu Leu Gly Asn Leu Phe Val Leu Val Phe Leu Leu Pro
                 50                  55                  60

Arg Arg Arg Leu Asn Val Ala Glu Ile Tyr Leu Ala Asn Leu Ala Ala
             65                  70                  75                  80

Ser Asp Leu Val Phe Val Leu Gly Leu Pro Phe Trp Ala Glu Asn Ile
                             85                  90                  95

Trp Asn Gln Phe Asn Trp Pro Phe Gly Ala Leu Leu Cys Arg Gly Ile
                            100                 105                 110

Asn Gly Val Ile Lys Ala Asn Leu Phe Ile Ser Ile Phe Leu Val Val
                        115                 120                 125

Ala Ile Ser Gln Asp Arg Tyr Cys Leu Leu Val His Pro Met Ala Ser
                        130                 135                 140

Arg Arg Arg Gln Arg Arg Gln Ala Arg Val Thr Cys Val Leu Ile
            145                 150                 155                 160

Trp Val Val Gly Gly Leu Leu Ser Ile Pro Thr Phe Leu Leu Arg Ser
                            165                 170                 175

Ile Gln Ala Val Pro Asp Leu Asn Ile Thr Ala Cys Ile Leu Leu Leu
                            180                 185                 190

Pro His Glu Ala Trp His Phe Ala Arg Ile Val Glu Leu Asn Ile Leu
                        195                 200                 205

Ala Phe Leu Leu Pro Leu Ala Ala Ile Val Phe Phe Asn Tyr His Ile
                        210                 215                 220

Leu Ala Ser Leu Arg Gly Arg Glu Glu Val Ser Arg Thr Arg Cys Gly
            225                 230                 235                 240

Gly Arg Lys Asp Ser Lys Thr Thr Ala Leu Ile Leu Thr Leu Val Val
                            245                 250                 255

Ala Phe Leu Val Cys Trp Ala Pro Tyr His Phe Phe Ala Phe Leu Glu
                        260                 265                 270

Phe Leu Phe Gln Val Gln Ala Ile Arg Ser Cys Phe Trp Glu Asp Phe
                        275                 280                 285

Ile Asp Leu Gly Leu Gln Leu Ala Asn Phe Leu Ala Phe Thr Asn Ser
                        290                 295                 300

Ser Leu Asn Pro Val Ile Tyr Val Phe Val Gly Arg Leu Phe Arg Thr
            305                 310                 315                 320

Lys Val Trp Glu Leu Tyr Lys Gln Cys Thr Pro Lys Ser Leu Ala Pro
                            325                 330                 335

Ile Ser Ser Ser His Arg Lys Glu Ile Phe Gln Leu Phe Trp Arg Asn
                        340                 345                 350

<210> SEQ ID NO 2
<211> LENGTH: 352
<212> TYPE: PRT
<213> ORGANISM: Macaca mulatta

<400> SEQUENCE: 2

Met Ala Ser Trp Pro Pro Leu Glu Leu Gln Ser Ser Asn Gln Ser Gln
             1               5                  10                  15

Leu Phe Pro Gln Asn Ala Thr Ala Cys Asp Asn Ala Pro Glu Ala Trp
                         20                  25                  30
```

```
Asp Leu Leu His Arg Val Leu Pro Thr Phe Ile Ile Ser Ile Cys Ser
            35                  40                  45

Phe Gly Leu Leu Gly Asn Leu Phe Val Leu Val Phe Leu Leu Pro
     50                  55                  60

Arg Arg Arg Leu Asn Val Ala Glu Ile Tyr Leu Ala Asn Leu Ala Ala
65                  70                  75                  80

Ser Asp Leu Val Phe Val Leu Gly Leu Pro Phe Trp Ala Glu Asn Ile
                85                  90                  95

Trp Asn Gln Phe Asn Trp Pro Phe Gly Ala Leu Leu Cys Arg Val Ile
                100                 105                 110

Asn Gly Ile Ile Lys Ala Asn Leu Phe Ile Ser Ile Phe Leu Val Val
            115                 120                 125

Ala Ile Ser Gln Asp Arg Tyr Cys Val Leu Val His Pro Met Ala Ser
    130                 135                 140

Arg Arg Arg Gln Arg Arg Arg Gln Ala Arg Val Thr Cys Val Leu Ile
145                 150                 155                 160

Trp Val Val Gly Gly Leu Leu Ser Ile Pro Thr Phe Leu Leu Arg Ser
                165                 170                 175

Ile Gln Ala Val Pro Asp Leu Asn Ile Thr Ala Cys Ile Leu Leu Leu
                180                 185                 190

Pro His Glu Ala Trp His Phe Ala Arg Ile Val Glu Leu Asn Ile Leu
            195                 200                 205

Ala Phe Leu Leu Pro Leu Ala Ala Ile Ile Phe Phe Asn Tyr His Ile
                210                 215                 220

Leu Ala Ser Leu Arg Gly Arg Glu Glu Val Ser Arg Thr Arg Cys Gly
225                 230                 235                 240

Gly Ser Lys Asp Ser Lys Thr Thr Ala Leu Ile Leu Thr Leu Val Val
                245                 250                 255

Ala Phe Leu Val Cys Trp Ala Pro Tyr His Phe Phe Ala Phe Leu Glu
                260                 265                 270

Phe Leu Phe Gln Val Gln Ala Val Arg Gly Cys Phe Trp Glu Asp Phe
            275                 280                 285

Ile Asp Leu Gly Leu Gln Leu Ala Asn Phe Leu Ala Phe Thr Asn Ser
    290                 295                 300

Ser Leu Asn Pro Val Ile Tyr Val Phe Val Gly Arg Leu Phe Arg Thr
305                 310                 315                 320

Lys Val Trp Glu Leu Tyr Lys Gln Cys Thr Pro Lys Ser Leu Ala Pro
                325                 330                 335

Ile Ser Ser Ser His Arg Lys Glu Ile Phe Gln Leu Phe Trp Arg Asn
                340                 345                 350

<210> SEQ ID NO 3
<211> LENGTH: 352
<212> TYPE: PRT
<213> ORGANISM: Tupaia minor

<400> SEQUENCE: 3

Met Ala Ala Gln Thr Leu Leu Glu Leu Gln Pro Ser Asn Gln Ser Gln
1               5                   10                  15

Leu Ser Ala Leu Asn Thr Thr Ser Cys Asp Asn Ala Arg Glu Ala Trp
            20                  25                  30

Asp Leu Leu Tyr Gln Val Leu Pro Ile Phe Ile Leu Thr Ile Cys Ala
            35                  40                  45

Phe Gly Leu Leu Gly Asn Leu Phe Val Leu Ser Val Phe Leu Leu Leu
     50                  55                  60
```

```
Arg Arg Arg Leu Thr Val Ala Glu Ile Tyr Leu Val Asn Leu Ala Ala
 65                  70                  75                  80

Ser Asp Leu Val Phe Val Leu Gly Leu Pro Phe Trp Ala Gln Asn Ile
                 85                  90                  95

Trp Asn Gln Phe Asn Trp Pro Phe Gly Asp Leu Leu Cys Arg Val Val
            100                 105                 110

Asn Gly Val Ile Lys Ala Asn Leu Phe Ile Ser Ile Phe Leu Met Val
        115                 120                 125

Ala Ile Ser Gln Asp Arg Tyr Cys Val Leu Val His Pro Met Ala Ser
130                 135                 140

Arg Arg Arg Arg Arg Arg Ala Arg Ala Thr Cys Met Val Ile
145                 150                 155                 160

Trp Ala Val Gly Ala Leu Leu Ser Thr Pro Thr Phe Leu Leu Arg Ser
                165                 170                 175

Val Ser Ala Val Gln Asp Leu Asn Ile Ser Ala Cys Ile Leu Leu Leu
            180                 185                 190

Pro His Gln Ala Trp His Val Ala Arg Ile Val Glu Leu Asn Val Leu
        195                 200                 205

Gly Phe Leu Leu Pro Leu Ala Ala Ile Ile Phe Phe Asn Gly His Ile
    210                 215                 220

Leu Ala Ser Leu Arg Gly Gln Gly Glu Val Ser Gln Thr Arg Ile Gly
225                 230                 235                 240

Gly Pro Lys Asp Cys Lys Thr Thr Val Leu Ile Leu Thr Leu Val Ala
                245                 250                 255

Ala Phe Leu Val Cys Trp Ala Pro Tyr His Cys Phe Ala Phe Leu Glu
            260                 265                 270

Phe Leu Phe Gln Val Arg Ala Val Arg Gly Cys Phe Trp Glu Asp Phe
        275                 280                 285

Ile Asp Leu Gly Leu Gln Leu Ala Asn Phe Phe Ala Phe Thr Asn Ser
    290                 295                 300

Cys Leu Asn Pro Val Ile Tyr Val Phe Val Gly Arg Leu Phe Arg Thr
305                 310                 315                 320

Lys Val Trp Glu Leu Tyr Gln Gln Cys Thr Pro Arg Arg Pro Ala Pro
                325                 330                 335

Leu Ser Ser Arg Arg Lys Glu Ile Leu Arg Arg Phe Trp Arg Asn
            340                 345                 350

<210> SEQ ID NO 4
<211> LENGTH: 320
<212> TYPE: PRT
<213> ORGANISM: Canis familiaris

<400> SEQUENCE: 4

Met Ala Ser Arg Ala Pro Leu Glu Leu Leu Pro Leu Asn Arg Ser Gln
  1               5                  10                  15

Leu Ser Pro Pro Asn Ala Thr Thr Cys Asp Asp Ala Pro Glu Ala Trp
                 20                  25                  30

Asp Leu Leu His Arg Val Leu Pro Ser Val Ile Ile Ile Cys Val
            35                  40                  45

Cys Gly Leu Leu Gly Asn Leu Val Leu Ala Val Leu Leu Arg Pro
         50                  55                  60

Arg Arg Arg Leu Asn Val Ala Glu Met Tyr Leu Ala Asn Leu Ala Ala
 65                  70                  75                  80

Ser Asp Leu Val Phe Val Leu Gly Leu Pro Phe Trp Ala Ala Asn Ile
```

-continued

```
                     85                  90                  95
Ser Asn Gln Phe Arg Trp Pro Phe Gly Gly Leu Leu Cys Arg Leu Val
            100                 105                 110
Asn Gly Val Ile Lys Ala Asn Leu Phe Ile Ser Ile Phe Leu Val Val
        115                 120                 125
Ala Ile Ser Arg Asp Arg Tyr Arg Ala Leu Val His Pro Met Ala Thr
    130                 135                 140
Arg Arg Arg Arg Gln Ala Arg Ala Thr Cys Val Leu Ile Trp Val Ala
145                 150                 155                 160
Gly Ser Leu Leu Ser Val Pro Thr Phe Leu Phe Arg Ser Ile Glu Ala
                165                 170                 175
Val Pro Glu Leu Asn Asn Asp Ser Ala Cys Val Leu His Pro Pro
            180                 185                 190
Gly Ala Trp His Val Ala Arg Met Val Glu Leu Asn Val Leu Gly Phe
        195                 200                 205
Leu Leu Pro Leu Ala Ala Ile Val Phe Asn Cys His Ile Leu Ala
    210                 215                 220
Ser Leu Arg Gly Arg Pro Glu Val Arg Gly Ala Arg Cys Gly Gly Pro
225                 230                 235                 240
Pro Asp Gly Arg Thr Thr Ala Leu Ile Leu Thr Phe Val Ala Ala Phe
                245                 250                 255
Leu Val Cys Trp Thr Pro Tyr His Phe Phe Ala Phe Leu Glu Phe Leu
            260                 265                 270
Thr Gln Val Gln Val Val Arg Gly Cys Phe Trp Glu Asn Phe Lys Asp
        275                 280                 285
Leu Gly Leu Gln Tyr Ala Ser Phe Phe Ala Phe Ile Asn Ser Cys Leu
    290                 295                 300
Asn Pro Val Ile Tyr Val Phe Val Gly Arg Leu Phe Arg Thr Lys Val
305                 310                 315                 320

<210> SEQ ID NO 5
<211> LENGTH: 350
<212> TYPE: PRT
<213> ORGANISM: Artificial Sequence
<220> FEATURE:
<223> OTHER INFORMATION: Description of Artificial Sequence:  chimeric
      molecule consisting of amino acids 1-320 of canine
      bradykinin B1 receptor (BKR) and amino acids
      319-353 of human BKR

<400> SEQUENCE: 5

Met Ala Ser Arg Ala Pro Leu Glu Leu Leu Pro Leu Asn Arg Ser Gln
1               5                   10                  15
Leu Ser Pro Pro Asn Ala Thr Thr Cys Asp Asp Ala Pro Glu Ala Trp
            20                  25                  30
Asp Leu Leu His Arg Val Leu Pro Ser Val Ile Ile Ile Cys Val
        35                  40                  45
Cys Gly Leu Leu Gly Asn Leu Leu Val Leu Ala Val Leu Leu Arg Pro
    50                  55                  60
Arg Arg Arg Leu Asn Val Ala Glu Met Tyr Leu Ala Asn Leu Ala Ala
65                  70                  75                  80
Ser Asp Leu Val Phe Val Leu Gly Leu Pro Phe Trp Ala Ala Asn Ile
                85                  90                  95
Ser Asn Gln Phe Arg Trp Pro Phe Gly Gly Leu Leu Cys Arg Leu Val
            100                 105                 110
Asn Gly Val Ile Lys Ala Asn Leu Phe Ile Ser Ile Phe Leu Val Val
```

```
            115                 120                 125
Ala Ile Ser Arg Asp Arg Tyr Arg Ala Leu Val His Pro Met Ala Thr
    130                 135                 140

Arg Arg Arg Arg Gln Ala Arg Ala Thr Cys Val Leu Ile Trp Val Ala
145                 150                 155                 160

Gly Ser Leu Leu Ser Val Pro Thr Phe Leu Phe Arg Ser Ile Glu Ala
                165                 170                 175

Val Pro Glu Leu Asn Asn Asp Ser Ala Cys Val Leu Leu His Pro Pro
            180                 185                 190

Gly Ala Trp His Val Ala Arg Met Val Glu Leu Asn Val Leu Gly Phe
        195                 200                 205

Leu Leu Pro Leu Ala Ala Ile Val Phe Phe Asn Cys His Ile Leu Ala
210                 215                 220

Ser Leu Arg Gly Arg Pro Glu Val Arg Gly Ala Arg Cys Gly Gly Pro
225                 230                 235                 240

Pro Asp Gly Arg Thr Thr Ala Leu Ile Leu Thr Phe Val Ala Ala Phe
                245                 250                 255

Leu Val Cys Trp Thr Pro Tyr His Phe Phe Ala Phe Leu Glu Phe Leu
                260                 265                 270

Thr Gln Val Gln Val Val Arg Gly Cys Phe Trp Glu Asn Phe Lys Asp
            275                 280                 285

Leu Gly Leu Gln Tyr Ala Ser Phe Phe Ala Phe Ile Asn Ser Cys Leu
        290                 295                 300

Asn Pro Val Ile Tyr Val Phe Val Gly Arg Leu Phe Arg Thr Lys Val
305                 310                 315                 320

Trp Glu Leu Tyr Lys Gln Cys Thr Pro Lys Ser Leu Ala Pro Ile Ser
                325                 330                 335

Ser Ser His Arg Lys Glu Ile Phe Gln Leu Phe Trp Arg Asn
                340                 345                 350

<210> SEQ ID NO 6
<211> LENGTH: 353
<212> TYPE: PRT
<213> ORGANISM: Sus sp.

<400> SEQUENCE: 6

Met Ala Ser Gln Thr Leu Val Val Phe Gln Ala Ser Asn Gln Ser Gln
1               5                   10                  15

Leu Pro Pro Pro Asn Ala Thr Leu Cys Asp Gly Ala Gln Glu Ala Trp
            20                  25                  30

His Leu Leu His Lys Val Leu Pro Thr Cys Val Val Ala Ile Cys Ser
        35                  40                  45

Gly Gly Leu Leu Gly Asn Leu Phe Val Leu Ser Val Phe Leu Val Pro
    50                  55                  60

Arg Arg Arg Leu Asn Ala Ala Glu Ile Tyr Leu Ala His Leu Ala Ala
65                  70                  75                  80

Ser Asp Leu Val Phe Ala Leu Gly Leu Pro Phe Trp Ala Glu Thr Ile
                85                  90                  95

Arg Asn Gly Phe His Trp Pro Phe Gly Ala Pro Leu Cys Arg Val Val
            100                 105                 110

Asn Gly Val Ile Lys Ala Asn Leu Phe Ile Ser Ile Phe Leu Val Val
        115                 120                 125

Ala Ile Ser Arg Asp Arg Tyr Arg Ala Leu Val His Pro Val Ala Ser
    130                 135                 140
```

-continued

```
Trp Arg Arg Arg Arg Arg His Trp Ala Gln Ala Thr Cys Val Leu
145                 150                 155                 160

Ile Trp Thr Ala Gly Gly Leu Leu Ser Ile Pro Thr Phe Leu Leu Arg
                165                 170                 175

Ser Val Gln Val Val Pro Glu Leu Asn Val Ser Ala Cys Val Leu Pro
            180                 185                 190

Phe Pro His Glu Ala Trp Ala Phe Val Arg Thr Val Glu Leu Asn Val
        195                 200                 205

Leu Gly Phe Leu Leu Pro Leu Ala Ala Ile Leu Phe Phe Asn Tyr His
    210                 215                 220

Ile Leu Ala Ala Leu Arg Gly Arg Glu Gln Leu Ser Arg Thr Arg Cys
225                 230                 235                 240

Gly Gly Pro Arg Asp Gly Lys Thr Thr Ala Leu Ile Leu Thr Leu Val
                245                 250                 255

Ala Val Phe Leu Leu Cys Trp Thr Pro Tyr His Val Cys Ala Phe Leu
                260                 265                 270

Glu Phe Leu Leu His Val Arg Ala Ile Arg Gly Cys Phe Trp Glu Asp
            275                 280                 285

Phe Thr Asp Leu Gly Leu Gln Tyr Thr Asn Phe Ala Phe Ile Asn
        290                 295                 300

Ser Cys Leu Asn Pro Val Ile Tyr Val Phe Trp Gly Gln Leu Phe Arg
305                 310                 315                 320

Thr Lys Ile Trp Glu Leu Tyr His Arg Cys Leu Pro Arg Lys Leu Thr
                325                 330                 335

Ala Val Ser Ser Ser Arg Arg Lys Glu Ile Phe Gln Ile Phe Trp Arg
                340                 345                 350

Asn
```

<210> SEQ ID NO 7
<211> LENGTH: 1059
<212> TYPE: DNA
<213> ORGANISM: Cercopithecus pygerythrus

<400> SEQUENCE: 7

```
atggcatcct ggccccctct agagctccag tcctccaacc agagccagct gttccctcaa      60
aatgctacag cctgtgacaa tgctccggaa gcctgggacc tgctgcacag agtgctgccg     120
acatttatca tctccatctg ttccttcggc ctcctaggga accttttcgt cctattggtc     180
ttcctcctgc ccaggcggcg actgaacgtg cagaaatct acctggccaa cctggcggcc     240
tctgatctgg tgtttgtctt gggcttgcct ttctgggcag agaatatttg gaaccagttt     300
aactggcctt tcggagccct cctctgccgt ggcatcaacg tgtcatcaa ggccaatttg     360
ttcatcagca tcttcctggt ggtggccatc agccaggacc gctactgcct gctggtgcac     420
cctatgcca gccggaggcg gcagcgacgg aggcaggccc gggtcacctg tgtgctcatc     480
tgggttgtgg gtggcctctt gagcatcccc acattcctgc tgcgatccat ccaagccgtc     540
ccagatctga acatcaccgc ctgcatcctg ctcctccccc atgaggcctg gcactttgca     600
aggattgtgg agttaaatat tctggctttc ctcctaccac tggctgcgat cgtcttcttc     660
aactaccaca tcttggcctc cctgcgaggg cgggaggagg tcagcaggac aaggtgcggg     720
ggccgcaagg atagcaagac cacagcgctg atcctcacgc tcgtggtggc cttcctggtc     780
tgctgggccc cttaccactt cttttgcctt ctgaattct tattccaggt gcaagcaatc     840
cgaagctgct tttgggagga cttcattgac ctgggcctgc aattggccaa cttcttggcc     900
```

| | |
|---|---|
| ttcaccaaca gctccctgaa tccagtcatt tatgtctttg tgggccggct cttcaggacc | 960 |
| aaggtctggg aactttataa acaatgcacc cctaaaagtc ttgctccaat atcttcatcc | 1020 |
| cacaggaaag aaatcttcca acttttctgg cggaattaa | 1059 |

<210> SEQ ID NO 8
<211> LENGTH: 1059
<212> TYPE: DNA
<213> ORGANISM: Macaca mulatta

<400> SEQUENCE: 8

| | |
|---|---|
| atggcatcct ggcccctct agagctccag tcctccaacc agagccagct gttccctcaa | 60 |
| aatgctacag cctgtgacaa tgctccagaa gcctgggacc tgctgcacag agtgctgccg | 120 |
| acatttatca tctccatctg ttccttcggc ctcctaggga accttttcgt cctgttggtc | 180 |
| ttcctcctgc ccaggcggcg actgaacgtg gcagaaatct acctggccaa cctggcggcc | 240 |
| tctgatctgt gtttgtctt gggtttgcct ttctgggcag agaacatttg gaaccagttt | 300 |
| aactggcctt tcggagccct cctctgccgt gtcatcaacg catcatcaa ggctaatttg | 360 |
| ttcatcagca tcttcctggt ggtggccatc agccaggacc gctactgcgt gctggtgcac | 420 |
| cctatggcca gccggaggcg gcagcggcgg aggcaggccc gggtcacctg cgtgctcatc | 480 |
| tgggttgtgg gggcctctt gagcatcccc acattcctgc tgcgatccat ccaagccgtc | 540 |
| ccagatctga acatcaccgc ctgcatcctg ctcctcccgc atgaggcctg gcactttgcg | 600 |
| aggattgtgg agttaaatat tctggctttc ctcctaccac tggctgcgat catcttcttc | 660 |
| aactaccaca tcttggcctc cctgcgaggg cgggaggagg tcagcaggac aaggtgcggg | 720 |
| ggcagcaagg atagcaagac cacagcgctg atcctcacgc tcgtggtggc cttcctggtc | 780 |
| tgctgggccc cttaccactt cttttgcctc ctggaattct tattccaggt gcaagcagtc | 840 |
| cgaggctgct tttgggagga cttcattgac ctgggcctgc aactggccaa cttcttggcc | 900 |
| ttcaccaaca gctccctgaa tccagtcatt tatgtctttg tgggccggct cttcaggacc | 960 |
| aaggtctggg aactttataa acaatgcacc cctaaaagtc ttgctccaat atcttcatcc | 1020 |
| cacaggaaag aaatcttcca acttttctgg cggaattaa | 1059 |

<210> SEQ ID NO 9
<211> LENGTH: 1059
<212> TYPE: DNA
<213> ORGANISM: Tupaia minor

<400> SEQUENCE: 9

| | |
|---|---|
| atggcagccc agacactcct ggaactccag ccctccaacc agagccagct gtccgctctc | 60 |
| aacaccacgt cctgtgacaa tgctcgggaa gcctgggacc tgctatacca agtgctacca | 120 |
| attttcatcc tcaccatctg cgccttcggc ctcctgggaa acctgttcgt cctgtctgtc | 180 |
| ttcctcctgc tcaggcgccg gctgactgtg cagaaatct acctggtcaa cctggcggct | 240 |
| tccgacctgg tgtttgtcct gggcttgccc ttctgggcac agaacatctg gaaccaattc | 300 |
| aactggcctt ttggggacct cctctgccgc gtcgtcaacg gagtcatcaa ggccaacttg | 360 |
| ttcatcagca tctttctgat ggtggccatc agccaggacc gctactgcgt gctggtgcat | 420 |
| cccatggcca gccgcaggcg gcggcggcgg cggcggccc gggccacctg catggtcatc | 480 |
| tgggccgtgg gggcctcct gagcaccccg acgttcctgc tgcgatccgt cagtgccgtc | 540 |
| caggatctga acatctctgc ctgcatcttg ctgcttccac accaggcctg gcacgtagcg | 600 |
| aggatcgtgg agctgaatgt gctggggttc ctcctgccct ggctgcaat catcttcttc | 660 |

```
aacggccaca tcctggcctc actgcgaggg caggggagg tcagccagac acggattggg      720
ggccccaagg actgcaagac caccgtgctg atcctcacgc tcgtggctgc tttcctggtc      780
tgctgggccc cctaccactg cttcgccttc ctggagttcc tgttccaggt gcagctgtg       840 cgaggctgct tctgggaaga cttcatcgac ctgggcctgc agctggccaa cttctttgct      900
ttcaccaaca gctgcctgaa cccggtgatc tatgtcttcg tgggccggct cttcaggacc      960
aaggtctggg aactgtacca acaatgcacc ccgagacgac cagctccccct gtcctcgtcc     1020 cgcaggaaag aaatcctccg gcgtttctgg cggaattaa                             1059

<210> SEQ ID NO 10
<211> LENGTH: 960
<212> TYPE: DNA
<213> ORGANISM: Canis familiaris

<400> SEQUENCE: 10
atggcatcgc gggcccccct ggagctcctg cccctgaacc ggagccagct gtcgcctcca       60
aacgccacga cctgtgacga tgctccagaa gcctgggacc tgctgcacag agtcttacca      120
tcagtcatca tcatcatctg tgtctgcggg ctgctgggaa accttctggt gctggcggtc      180
ttgctccggc cccggcggcg tctgaacgtg gccgaaatgt acctggccaa cctggccgcc      240
tccgacctgg tgtttgtcct gggcttgccc ttctgggcgg cgaacatctc gaaccagttc      300
cgctggccct cgggggcct cctctgccgc ctcgtcaacg gagtcatcaa ggccaatttg       360
ttcatcagca tcttcctggt ggtggccatc agccggacc gctaccgcgc gctggtgcac       420
cccatggcca cccggcggcg gcgacaggcc cgggccacct gcgtgctcat ctgggtggcg      480
ggcagcctcc tgagcgtccc caccttcctg ttccgctcca tcgaagctgt gcccgagctg      540
aacaacgaca gcgcctgcgt cctgctgcac ccgcccgggg cctggcacgt cgcgaggatg      600
gtggagctga acgtgctggg gttcctgctg ccgctggctg ccatcgtctt cttcaactgc      660
cacatcctgg cctccctgcg cgggcggccc gaggtgcgcg gggcgcggtg cgggggcccc      720
cccgacggca ggaccacggc gctcatcctc accttcgtgg ccgccttcct ggtgtgctgg      780 acccctacc acttcttcgc cttcctggaa ttcctgacgc aggtgcaggt cgtccgcggc      840
tgcttctggg agaatttcaa agacctgggc ctgcagtacg ccagcttctt tgccttcatc      900
aacagctgcc tgaaccccgt catctacgtc ttcgtgggcc ggctcyttaa gaccarggty      960

<210> SEQ ID NO 11
<211> LENGTH: 1053
<212> TYPE: DNA
<213> ORGANISM: Artificial Sequence
<220> FEATURE:
<223> OTHER INFORMATION: Description of Artificial Sequence:  chimeric
      DNA comprising nucleotides 1-945 of dog BKR and
      nucleotides 946-1053 of human BKR

<400> SEQUENCE: 11
atggcatcgc gggcccccct ggagctcctg cccctgaacc ggagccagct gtcgcctcca       60
aacgccacga cctgtgacga tgctccagaa gcctgggacc tgctgcacag agtcttacca      120
tcagtcatca tcatcatctg tgtctgcggg ctgctgggaa accttctggt gctggcggtc      180
ttgctccggc cccggcggcg tctgaacgtg gccgaaatgt acctggccaa cctggccgcc      240
tccgacctgg tgtttgtcct gggcttgccc ttctgggcgg cgaacatctc gaaccagttc      300
cgctggccct cgggggcct cctctgccgc ctcgtcaacg gagtcatcaa ggccaatttg       360
```

```
ttcatcagca tcttcctggt ggtggccatc agccgggacc gctaccgcgc gctggtgcac    420
cccatggcca cccggcggcg gcgacaggcc cgggccacct gcgtgctcat ctgggtggcg    480
ggcagcctcc tgagcgtccc caccttcctg ttccgctcca tcgaagctgt gcccgagctg    540
aacaacgaca gcgcctgcgt cctgctgcac ccgcccgggg cctggcacgt cgcgaggatg    600
gtggagctga acgtgctggg gttcctgctg ccgctggctg ccatcgtctt cttcaactgc    660
cacatcctgg cctccctgcg cgggcggccc gaggtgcgcg gggcgcggtg cgggggggccc    720 cccgacggca ggaccacggc gctcatcctc accttcgtgg ccgccttcct ggtgtgctgg    780
accccctacc acttcttcgc cttcctggaa ttcctgacgc aggtgcaggt cgtccgcggc    840
tgcttctggg agaatttcaa agacctgggc ctgcagtacg ccagcttctt tgccttcatc    900
aacagctgcc tgaaccccgt catctacgtc ttcgtgggcc ggctcttcag gaccaaggtc    960
tgggaacttt ataaacaatg caccccctaaa agtcttgctc caatatcttc atcccatagg   1020
aaagaaatct tccaactttt ctggcggaat taa                                 1053

<210> SEQ ID NO 12
<211> LENGTH: 1062
<212> TYPE: DNA
<213> ORGANISM: Sus sp.

<400> SEQUENCE: 12
atggcctccc agaccctcgt ggtgttccag gcctccaacc agagccagct cccacctcca     60
aatgccacgc tgtgtgacgg tgctcaggaa gcctggcacc tgctgcacaa ggtgctaccg    120
acttgcgtcg tggccatctg ctcgggcggc ctgctgggaa acctcttcgt gctgtcggtc    180
ttcctcgtgc ctcgacggcg tctgaacgcg gcggaaatct acctggccca cctgccgct    240 tctgacctgg tgttcgcctt gggcttgccc ttctgggccg agaccatccg gaacggattc    300
cactggcctt tcggagcccc cctctgccgc gtggtcaacg cgtcatcaa ggccaacctg    360 ttcatcagca tcttcctggt ggtggccatc agccgggacc gctaccgcgc gctggtgcac    420
cccgtggcca gctggaggcg gcggcggcgg cgccactggg cccaggccac ctgcgtgctc    480
atctggacgg cggggggcct cctgagcatc cccacgttcc tgctgcgctc cgtccaagtg    540
gtcccggagc tgaacgtctc cgcctgcgtg ctgcccttcc ccacgaggc ctgggccttc    600 gtcaggacgg tggagttgaa cgtgctgggc tttctcctcc cgctggctgc catcctcttc    660
ttcaactatc acatcctggc agccctgcgg gggcgggagc agctcagcag gacaaggtgc    720
gggggcccca gggatggcaa gaccacgcg ctgatcctca cgctcgtggc cgtcttcctg    780
ctctgctgga ccccgtacca cgtctgtgcc ttcctggaat tcctgctcca cgtgcgggcc    840
atccgaggct gcttctggga ggatttcacc gacctgggct tgcagtacac caacttcttt    900
gctttcatca acagctgcct aaatccagtc atctacgtct tttggggcca gcttttcaga    960
accaagatct gggaactgta tcaccgatgc ctccccagaa agctcactgc cgtgtcctcg   1020
tcccgtagga aagaaatctt ccaaattttc tggcggaatt aa                       1062

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:sense primer
<220> FEATURE:
<223> OTHER INFORMATION: y can be T or C
<220> FEATURE:
<223> OTHER INFORMATION: m can be A or C
```

```
<220> FEATURE:
<223> OTHER INFORMATION: k can be G or T
<220> FEATURE:
<223> OTHER INFORMATION: r can be G or A
<220> FEATURE:
<223> OTHER INFORMATION: s can be G or C

<400> SEQUENCE: 13
tgtycmkkyc rrgtcactgt gsatggc                                       27

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:antisense
      primer
<220> FEATURE:
<223> OTHER INFORMATION: y can be T or C

<400> SEQUENCE: 14
gctgytttaa ttccgccaga a                                             21

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:sense primer

<400> SEQUENCE: 15
ggactagtac caccatggca tcatcctggc                                    30

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:antisense
      primer

<400> SEQUENCE: 16
gcgtcgacgg ttcaatgctg ttttaattcc gcc                                33

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence:sense primer

<400> SEQUENCE: 17
gcatgccacc atggcgtccg aggtcttgtt g                                  31

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:antisense
      primer

<400> SEQUENCE: 18
tgacttataa agtccccaga accctg                                        26

<210> SEQ ID NO 19
<211> LENGTH: 39
```

<212> TYPE: DNA
<213> ORGANISM: Artificial Sequence
<220> FEATURE:
<223> OTHER INFORMATION: Description of Artificial Sequence:sense primer

<400> SEQUENCE: 19
ataggtaccg ccaccatggc atcctggccc cctctagag        39

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:antisense
      primer

<400> SEQUENCE: 20
gcgctcgagg ctgttttaat tccgccagaa        30

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:sense primer

<400> SEQUENCE: 21
ataggtaccg ccaccatggc agcccagaca ctcctg        36

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence:antisense
      primer

<400> SEQUENCE: 22
gcgctcgagt taattccgcc agaaamgcc        29

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence:sense primer

<400> SEQUENCE: 23
ataggtaccg ccaccatggc ctcccagacc ctcgtg        36

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:antisense
      primer

<400> SEQUENCE: 24
gcgctcgagg ctgttttaat tccgccagaa        30

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence:sense primer -continued

<400> SEQUENCE: 25
ataggtaccg ccaccatggc atcgcgggcc cccctg                                   36

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:antisense
      primer

<400> SEQUENCE: 26
raccytggtc ytrargagcc ggcc                                                24

<210> SEQ ID NO 27
<211> LENGTH: 355
<212> TYPE: PRT
<213> ORGANISM: Homo sapiens

<400> SEQUENCE: 27

Met Glu Ser Asp Ser Phe Glu Asp Phe Trp Lys Gly Glu Asp Leu Ser
1               5                   10                  15

Asn Tyr Ser Tyr Ser Ser Thr Leu Pro Pro Phe Leu Leu Asp Ala Ala
                20                  25                  30

Pro Cys Glu Pro Glu Ser Leu Glu Ile Asn Lys Tyr Phe Val Val Ile
            35                  40                  45

Ile Tyr Ala Leu Val Phe Leu Leu Ser Leu Leu Gly Asn Ser Leu Val
    50                  55                  60

Met Leu Val Ile Leu Tyr Ser Arg Val Gly Arg Ser Val Thr Asp Val
65                  70                  75                  80

Tyr Leu Leu Asn Leu Ala Leu Ala Asp Leu Leu Phe Ala Leu Thr Leu
                85                  90                  95

Pro Ile Trp Ala Ala Ser Lys Val Asn Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
    130                 135                 140

His Ala Thr Arg Thr Leu Thr Gln Lys Arg Tyr Leu Val Lys Phe Ile
145                 150                 155                 160

Cys Leu Ser Ile Trp Gly Leu Ser Leu Leu Ala Leu Pro Val Leu
                165                 170                 175

Leu Phe Arg Arg Thr Val Tyr Ser Ser Asn Val Ser Pro Ala Cys Tyr
            180                 185                 190

Glu Asp Met Gly Asn Asn Thr Ala Asn Trp Arg Met Leu Leu Arg Ile
        195                 200                 205

Leu Pro Gln Ser Phe Gly Phe Ile Val Pro Leu Leu Ile Met Leu Phe
    210                 215                 220

Cys Tyr Gly Phe Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr Asn Leu Val Leu Leu Ala Asp Thr Leu Met
            260                 265                 270

Arg Thr Gln Val Ile Gln Glu Thr Cys Glu Arg Arg Asn His Ile Asp
        275                 280                 285

```
Arg Ala Leu Asp Ala Thr Glu Ile Leu Gly Ile Leu His Ser Cys Leu
    290                 295                 300

Asn Pro Leu Ile Tyr Ala Phe Ile Gly Gln Lys Phe Arg His Gly Leu
305                 310                 315                 320

Leu Lys Ile Leu Ala Ile His Gly Leu Ile Ser Lys Asp Ser Leu Pro
                325                 330                 335

Lys Asp Ser Arg Pro Ser Phe Val Gly Ser Ser Ser Gly His Thr Ser
            340                 345                 350

Thr Thr Leu
        355

<210> SEQ ID NO 28
<211> LENGTH: 355
<212> TYPE: PRT
<213> ORGANISM: Pan troglodytes

<400> SEQUENCE: 28

Met Glu Ser Asp Ser Phe Glu Asp Phe Trp Lys Gly Glu Asp Leu Ser
1               5                   10                  15

Asn Tyr Ser Tyr Ser Ser Thr Leu Pro Pro Phe Leu Leu Asp Ala Ala
                20                  25                  30

Pro Cys Glu Pro Glu Ser Leu Glu Ile Asn Lys Tyr Phe Val Val Ile
            35                  40                  45

Ile Tyr Ala Leu Val Phe Leu Leu Ser Leu Leu Gly Asn Ser Leu Val
        50                  55                  60

Met Leu Val Ile Leu Tyr Ser Arg Val Gly Arg Ser Val Thr Asp Val
65                  70                  75                  80

Tyr Leu Leu Asn Leu Ala Leu Ala Asp Leu Leu Phe Ala Leu Thr Leu
                85                  90                  95

Pro Ile Trp Ala Ala Ser Lys Val Asn Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
        130                 135                 140

His Ala Thr Arg Thr Leu Thr Gln Lys Arg Tyr Leu Val Lys Phe Ile
145                 150                 155                 160

Cys Leu Ser Ile Trp Gly Leu Ser Leu Leu Leu Ala Leu Pro Val Leu
                165                 170                 175

Leu Phe Arg Arg Thr Val Tyr Ser Ser Asn Val Ser Pro Ala Cys Tyr
            180                 185                 190

Glu Asp Met Gly Asn Asn Thr Ala Asn Trp Arg Met Leu Leu Arg Ile
        195                 200                 205

Leu Pro Gln Ser Phe Gly Phe Ile Val Pro Leu Leu Ile Met Leu Phe
    210                 215                 220

Cys Tyr Gly Phe Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr Asn Leu Val Leu Leu Ala Asp Thr Leu Met
            260                 265                 270

Arg Thr Gln Val Ile Gln Glu Thr Cys Glu Arg Arg Asn His Ile Asp
        275                 280                 285

Arg Ala Leu Asp Ala Thr Glu Ile Leu Gly Ile Leu His Ser Cys Leu
```

```
            290                 295                 300
Asn Pro Leu Ile Tyr Ala Phe Ile Gly Gln Lys Phe Arg His Gly Leu
305                 310                 315                 320

Leu Lys Ile Leu Ala Ile His Gly Leu Ile Ser Lys Asp Ser Leu Pro
                325                 330                 335

Lys Asp Ser Arg Pro Ser Phe Val Gly Ser Ser Ser Gly His Thr Ser
            340                 345                 350

Thr Thr Leu
        355

<210> SEQ ID NO 29
<211> LENGTH: 355
<212> TYPE: PRT
<213> ORGANISM: Pan troglodytes

<400> SEQUENCE: 29

Met Glu Ser Asp Ser Phe Glu Asp Phe Trp Lys Gly Glu Asp Leu Ser
1               5                   10                  15

Asn Tyr Ser Tyr Ser Ser Thr Leu Pro Pro Phe Leu Leu Asp Ala Ala
                20                  25                  30

Pro Cys Glu Pro Glu Ser Leu Glu Ile Asn Lys Tyr Phe Val Val Ile
            35                  40                  45

Ile Tyr Ala Leu Val Phe Leu Leu Ser Leu Leu Gly Asn Ser Leu Val
        50                  55                  60

Met Leu Val Ile Leu Tyr Ser Arg Val Gly Arg Ser Val Thr Asp Val
65                  70                  75                  80

Tyr Leu Leu Asn Leu Ala Leu Ala Asp Leu Leu Phe Ala Leu Thr Leu
                85                  90                  95

Pro Ile Trp Ala Ala Ser Lys Val Asn Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
    130                 135                 140

His Ala Thr Arg Thr Leu Thr Gln Lys Arg Tyr Leu Val Lys Phe Ile
145                 150                 155                 160

Cys Leu Ser Ile Trp Gly Leu Ser Leu Leu Ala Leu Pro Val Leu
                165                 170                 175

Leu Phe Arg Arg Thr Val Tyr Ser Ser Asn Val Ser Pro Ala Cys Tyr
            180                 185                 190

Glu Asp Met Gly Asn Asn Thr Ala Asn Trp Arg Met Leu Leu Arg Met
        195                 200                 205

Leu Pro Gln Ser Phe Gly Phe Ile Val Pro Leu Leu Ile Met Leu Phe
    210                 215                 220

Cys Tyr Gly Phe Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr Asn Leu Val Leu Leu Ala Asp Thr Leu Met
            260                 265                 270

Arg Thr Gln Val Ile Gln Glu Thr Cys Glu Arg Arg Asn His Ile Asn
        275                 280                 285

Arg Ala Leu Asp Ala Thr Glu Ile Leu Gly Ile Leu His Ser Cys Leu
    290                 295                 300
```

```
Asn Pro Leu Ile Tyr Ala Phe Ile Gly Gln Lys Phe Arg His Gly Leu
305                 310                 315                 320

Leu Lys Ile Leu Ala Ile His Gly Leu Ile Ser Lys Asp Ser Leu Pro
            325                 330                 335

Lys Asp Ser Arg Pro Ser Phe Val Gly Ser Ser Ser Gly His Thr Ser
            340                 345                 350

Thr Thr Leu
        355

<210> SEQ ID NO 30
<211> LENGTH: 355
<212> TYPE: PRT
<213> ORGANISM: Gorilla gorilla

<400> SEQUENCE: 30

Met Glu Ser Asp Ser Phe Glu Asp Phe Trp Lys Gly Glu Asp Leu Ser
1               5                   10                  15

Asn Tyr Ser Tyr Ser Ser Asp Leu Pro Pro Phe Leu Leu Asp Ala Ser
            20                  25                  30

Pro Cys Glu Pro Glu Ser Leu Glu Ile Asn Lys Tyr Phe Val Val Ile
            35                  40                  45

Ile Tyr Ala Leu Val Phe Leu Leu Ser Leu Leu Gly Asn Ser Leu Val
50                  55                  60

Ile Leu Val Ile Leu Tyr Ser Arg Val Gly Arg Ser Val Thr Asp Val
65                  70                  75                  80

Tyr Leu Leu Asn Leu Ala Leu Ala Asp Leu Leu Phe Ala Leu Thr Leu
                85                  90                  95

Pro Ile Trp Ala Ala Ser Lys Val Asn Gly Trp Ile Phe Gly Thr Phe
            100                 105                 110

Leu Cys Lys Val Val Ser Leu Leu Lys Glu Val Asn Phe Tyr Ser Gly
            115                 120                 125

Ile Leu Leu Leu Ala Cys Ile Ser Val Asp Arg Tyr Leu Ala Ile Val
            130                 135                 140

His Ala Thr Arg Thr Leu Thr Gln Lys Arg Tyr Leu Val Lys Phe Ile
145                 150                 155                 160

Cys Leu Ser Ile Trp Gly Leu Ser Leu Leu Leu Ala Leu Pro Val Leu
                165                 170                 175

Leu Phe Arg Arg Thr Ile Tyr Pro Ser Asn Val Ser Pro Val Cys Tyr
            180                 185                 190

Glu Asp Met Gly Asn Asn Thr Ala Asn Trp Arg Met Leu Leu Arg Ile
            195                 200                 205

Leu Pro Gln Ser Phe Gly Phe Ile Val Pro Leu Leu Ile Met Leu Phe
210                 215                 220

Cys Tyr Gly Phe Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr Asn Leu Val Leu Leu Ala Asp Thr Leu Met
            260                 265                 270

Arg Thr Gln Val Ile Gln Glu Thr Cys Glu Arg Arg Asn His Ile Asp
            275                 280                 285

Arg Ala Leu Asp Ala Thr Glu Ile Leu Gly Ile Leu His Ser Cys Leu
            290                 295                 300

Asn Pro Leu Ile Tyr Ala Phe Ile Gly Gln Lys Phe Arg His Gly Leu
305                 310                 315                 320
```

```
Leu Lys Ile Leu Ala Ile His Gly Leu Ile Ser Lys Asp Ser Leu Pro
                325                 330                 335

Lys Asp Ser Arg Pro Ser Phe Val Gly Ser Ser Ser Gly His Thr Ser
            340                 345                 350

Thr Thr Leu
        355

<210> SEQ ID NO 31
<211> LENGTH: 355
<212> TYPE: PRT
<213> ORGANISM: Gorilla gorilla

<400> SEQUENCE: 31

Met Glu Ser Asp Ser Phe Glu Asp Phe Trp Lys Gly Glu Asp Leu Ser
1               5                   10                  15

Asn Tyr Ser Tyr Ser Ser Ala Leu Pro Pro Phe Leu Leu Asp Ala Ser
            20                  25                  30

Pro Cys Glu Pro Glu Ser Leu Glu Ile Asn Lys Tyr Phe Val Val Ile
        35                  40                  45

Ile Tyr Ala Leu Val Phe Leu Leu Ser Leu Leu Gly Asn Ser Leu Val
    50                  55                  60

Ile Leu Val Ile Leu Tyr Ser Arg Val Gly Arg Ser Val Thr Asp Val
65                  70                  75                  80

Tyr Leu Leu Asn Leu Ala Leu Ala Asp Leu Leu Phe Ala Leu Thr Leu
                85                  90                  95

Pro Ile Trp Ala Ala Ser Lys Val Asn Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
    130                 135                 140

His Ala Thr Arg Thr Leu Thr Gln Lys Arg Tyr Leu Val Lys Phe Ile
145                 150                 155                 160

Cys Leu Ser Ile Trp Gly Leu Ser Leu Leu Leu Ala Leu Pro Val Leu
                165                 170                 175

Leu Phe Arg Arg Thr Ile Tyr Pro Ser Asn Val Ser Pro Val Cys Tyr
            180                 185                 190

Glu Asp Met Gly Asn Asn Thr Ala Asn Trp Arg Met Leu Leu Arg Ile
        195                 200                 205

Leu Pro Gln Ser Phe Gly Phe Ile Val Pro Leu Leu Ile Met Leu Phe
    210                 215                 220

Cys Tyr Gly Phe Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr Asn Leu Val Leu Leu Ala Asp Thr Leu Met
            260                 265                 270

Arg Thr Gln Val Ile Gln Glu Thr Cys Glu Arg Arg Asn His Ile Asn
        275                 280                 285

Gln Ala Leu Asp Ala Thr Glu Ile Leu Gly Ile Leu His Ser Cys Leu
    290                 295                 300

Asn Pro Leu Ile Tyr Ala Phe Ile Gly Gln Lys Phe Cys His Gly Leu
305                 310                 315                 320

Leu Lys Ile Leu Ala Ile His Gly Leu Ile Ser Lys Asp Ser Leu Pro
```

Lys Asp Ser Arg Pro Ser Phe Val Gly Ser Ser Ser Gly His Thr Ser
            325                 330                 335
            340                 345                 350

Thr Thr Leu
        355

<210> SEQ ID NO 32
<211> LENGTH: 355
<212> TYPE: PRT
<213> ORGANISM: Pongo pygmaeus

<400> SEQUENCE: 32

Met Glu Ser Asp Ser Phe Glu Asp Phe Leu Lys Gly Glu Asp Phe Ser
1               5                   10                  15

Asn Tyr Ser Tyr Ser Ser Asp Leu Pro Phe Leu Leu Asp Ala Ala
            20                  25                  30

Pro Cys Glu Pro Glu Ser Leu Glu Ile Asn Lys Tyr Phe Val Val Ile
            35                  40                  45

Ile Tyr Val Leu Val Phe Leu Leu Ser Leu Leu Gly Asn Ser Leu Val
        50                  55                  60

Met Leu Val Ile Leu Tyr Ser Arg Val Gly Arg Ser Val Thr Asp Val
65                  70                  75                  80

Tyr Leu Leu Asn Leu Ala Leu Ala Asp Leu Leu Phe Ala Leu Thr Leu
                85                  90                  95

Pro Ile Trp Ala Ala Ser Lys Val Thr Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
    130                 135                 140

His Ala Thr Arg Thr Leu Thr Gln Lys Arg Tyr Leu Val Lys Phe Ile
145                 150                 155                 160

Cys Leu Ser Ile Trp Gly Leu Ser Leu Leu Leu Ala Leu Pro Val Leu
                165                 170                 175

Ile Phe Arg Lys Thr Ile Tyr Pro Pro Tyr Val Ser Pro Val Cys Tyr
            180                 185                 190

Glu Asp Met Gly Asn Asn Thr Ala Asn Trp Arg Met Leu Leu Arg Ile
        195                 200                 205

Leu Pro Gln Ser Phe Gly Phe Ile Val Pro Leu Leu Ile Met Leu Phe
    210                 215                 220

Cys Tyr Gly Phe Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr Asn Leu Val Leu Leu Ala Asp Thr Leu Met
            260                 265                 270

Arg Thr Trp Val Ile Gln Glu Thr Cys Glu Arg Arg Asn Asp Ile Asp
        275                 280                 285

Arg Ala Leu Glu Ala Thr Glu Ile Leu Gly Ile Leu His Ser Cys Leu
    290                 295                 300

Asn Pro Leu Ile Tyr Ala Phe Ile Gly Gln Lys Phe Arg His Gly Leu
305                 310                 315                 320

Leu Lys Ile Leu Ala Ile His Gly Leu Ile Ser Lys Asp Ser Leu Pro
                325                 330                 335

Lys Asp Ser Arg Pro Ser Phe Val Gly Ser Ser Ser Gly His Thr Ser
            340                 345                 350

Thr Thr Leu
        355

<210> SEQ ID NO 33
<211> LENGTH: 355
<212> TYPE: PRT
<213> ORGANISM: Pongo pygmaeus

<400> SEQUENCE: 33

Met Glu Ser Asp Ser Phe Glu Asp Phe Trp Lys Gly Glu Asp Leu Ser
1               5                   10                  15

Asn Tyr Ser Tyr Ser Ser Thr Leu Pro Pro Phe Leu Leu Asp Ala Ala
            20                  25                  30

Pro Cys Glu Pro Glu Ser Leu Glu Ile Asn Lys Tyr Phe Val Val Ile
        35                  40                  45

Ile Tyr Val Leu Val Phe Leu Leu Ser Leu Leu Gly Asn Ser Leu Val
    50                  55                  60

Met Leu Val Ile Leu Tyr Ser Arg Val Gly Arg Ser Val Thr Asp Val
65                  70                  75                  80

Tyr Leu Leu Asn Leu Ala Leu Ala Asp Leu Leu Phe Ala Leu Thr Leu
                85                  90                  95

Pro Ile Trp Ala Ala Ser Lys Val Thr Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
    130                 135                 140

His Ala Thr Arg Thr Leu Thr Gln Lys Arg Tyr Leu Val Lys Phe Ile
145                 150                 155                 160

Cys Leu Ser Ile Trp Gly Leu Ser Leu Leu Leu Ala Leu Pro Val Leu
                165                 170                 175

Ile Phe Arg Lys Thr Ile Tyr Pro Ser Tyr Val Ser Pro Val Cys Tyr
            180                 185                 190

Glu Asp Met Gly Asn Asn Thr Ala Asn Trp Arg Met Leu Leu Arg Ile
        195                 200                 205

Leu Pro Gln Ser Phe Gly Phe Ile Val Pro Leu Leu Ile Met Leu Phe
    210                 215                 220

Cys Tyr Gly Phe Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr Asn Leu Val Leu Leu Ala Asp Thr Leu Met
            260                 265                 270

Arg Asn Gln Met Ile Asn Glu Thr Cys Glu Arg Cys Asn His Ile Asn
        275                 280                 285

Gln Ala Leu Asp Ala Thr Glu Ile Leu Gly Ile Leu His Ser Cys Leu
    290                 295                 300

Asn Pro Leu Ile Tyr Ala Phe Ile Gly Gln Lys Phe Arg His Gly Leu
305                 310                 315                 320

Leu Lys Ile Leu Val Ile His Gly Leu Ile Ser Lys Asp Ser Leu Pro
                325                 330                 335

Lys Asp Ser Arg Pro Ser Phe Val Gly Ser Ser Ser Gly His Thr Ser
            340                 345                 350

Thr Thr Leu
        355

<210> SEQ ID NO 34
<211> LENGTH: 355
<212> TYPE: PRT
<213> ORGANISM: Macaca mulatta

<400> SEQUENCE: 34

Met Glu Ser Phe Asn Phe Glu Asp Leu Trp Lys Gly Glu Asp Phe Ser
1               5                   10                  15

Asn Tyr Ser Tyr Ser Ser Asp Leu Pro Pro Ser Leu Pro Asp Val Ala
            20                  25                  30

Pro Cys Arg Pro Glu Ser Leu Glu Ile Asn Lys Tyr Phe Val Val Ile
        35                  40                  45

Ile Tyr Val Leu Val Phe Leu Leu Ser Leu Leu Gly Asn Ser Leu Val
    50                  55                  60

Met Leu Val Ile Leu His Ser Arg Val Gly Arg Ser Ile Thr Asp Val
65                  70                  75                  80

Tyr Leu Leu Asn Leu Ala Met Ala Asp Leu Leu Phe Ala Leu Thr Leu
                85                  90                  95

Pro Ile Trp Ala Ala Lys Val Asn Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
    130                 135                 140

His Ala Thr Arg Thr Leu Thr Gln Lys Arg Tyr Leu Val Lys Phe Val
145                 150                 155                 160

Cys Leu Ser Ile Trp Ser Leu Ser Leu Leu Ala Leu Pro Val Leu
                165                 170                 175

Leu Phe Arg Arg Thr Val Tyr Leu Thr Tyr Ile Ser Pro Val Cys Tyr
            180                 185                 190

Glu Asp Met Gly Asn Asn Thr Ala Lys Trp Arg Met Val Leu Arg Ile
        195                 200                 205

Leu Pro Gln Thr Phe Gly Phe Ile Leu Pro Leu Leu Ile Met Leu Phe
    210                 215                 220

Cys Tyr Gly Leu Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr His Leu Val Leu Leu Ala Asp Thr Leu Met
            260                 265                 270

Arg Thr Arg Leu Ile Asn Glu Thr Cys Gln Arg Arg Asn Asn Ile Asp
        275                 280                 285

Gln Ala Leu Asp Ala Thr Glu Ile Leu Gly Ile Leu His Ser Cys Leu
    290                 295                 300

Asn Pro Leu Ile Tyr Ala Phe Ile Gly Gln Lys Phe Arg His Gly Leu
305                 310                 315                 320

Leu Lys Ile Leu Ala Thr His Gly Leu Ile Ser Lys Asp Ser Leu Pro
                325                 330                 335

Lys Asp Ser Arg Pro Ser Phe Val Gly Ser Ser Ser Gly His Thr Ser
            340                 345                 350

Thr Thr Leu

<210> SEQ ID NO 35
<211> LENGTH: 355
<212> TYPE: PRT
<213> ORGANISM: Macaca mulatta

<400> SEQUENCE: 35

```
Met Glu Ser Asp Ser Phe Glu Asp Leu Trp Lys Gly Glu Asp Phe Ser
1               5                   10                  15

Asn Tyr Ser Tyr Ser Ser Asp Leu Pro Pro Ser Leu Pro Asp Val Ala
            20                  25                  30

Pro Cys Arg Pro Glu Ser Leu Glu Ile Asn Lys Tyr Phe Val Val Ile
        35                  40                  45

Ile Tyr Val Leu Val Phe Leu Leu Ser Leu Leu Gly Asn Ser Leu Val
    50                  55                  60

Met Leu Val Ile Leu Tyr Ser Arg Val Gly Arg Ser Val Thr Asp Val
65                  70                  75                  80

Tyr Leu Leu Asn Leu Ala Leu Ala Asp Leu Leu Phe Ala Leu Thr Leu
                85                  90                  95

Pro Ile Trp Ala Ala Ser Lys Val Asn Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
    130                 135                 140

His Ala Thr Arg Thr Leu Thr Gln Lys Arg Tyr Leu Val Lys Phe Ile
145                 150                 155                 160

Cys Leu Ser Ile Trp Gly Leu Ser Leu Leu Leu Ala Leu Pro Val Leu
                165                 170                 175

Leu Phe Arg Arg Thr Val Tyr Ser Ser Asn Val Ser Pro Ala Cys Tyr
            180                 185                 190

Glu Asp Met Gly Asn Asn Thr Ala Asn Trp Arg Met Leu Leu Arg Ile
        195                 200                 205

Leu Pro Gln Ser Phe Gly Phe Ile Val Pro Leu Leu Ile Met Leu Phe
    210                 215                 220

Cys Tyr Gly Phe Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr Ser Leu Val Leu Leu Ala Asp Thr Leu Met
            260                 265                 270

Arg Thr Gln Val Ile Gln Glu Thr Cys Glu Arg Arg Asn His Ile Asp
        275                 280                 285

Arg Ala Leu Asp Ala Thr Glu Ile Leu Gly Ile Leu His Ser Cys Leu
    290                 295                 300

Asn Pro Leu Ile Tyr Ala Phe Ile Gly Gln Lys Phe Arg His Gly Leu
305                 310                 315                 320

Leu Lys Ile Leu Ala Ile His Gly Leu Ile Ser Lys Asp Ser Leu Pro
                325                 330                 335

Lys Asp Ser Arg Pro Ser Phe Val Gly Ser Ser Gly His Thr Ser
            340                 345                 350

Thr Thr Leu
        355
```

```
<210> SEQ ID NO 36
<211> LENGTH: 355
<212> TYPE: PRT
<213> ORGANISM: Cercopithecus pygerythrus

<400> SEQUENCE: 36

Met Glu Ile Ser Asn Phe Glu Asp Leu Trp Lys Ser Glu Asp Phe Ser
1               5                   10                  15

Asn Tyr Ser Tyr Ser Ser Asp Leu Pro Pro Ser Leu Pro Asp Val Thr
            20                  25                  30

Pro Cys Arg Pro Glu Ser Leu Glu Ile Asn Lys Tyr Phe Val Val Ile
        35                  40                  45

Ile Tyr Val Leu Val Phe Leu Leu Ser Leu Leu Gly Asn Ser Leu Val
    50                  55                  60

Met Leu Val Ile Leu His Ser Arg Val Gly Arg Ser Val Thr Asp Val
65                  70                  75                  80

Tyr Leu Leu Asn Leu Ala Met Ala Asp Leu Leu Phe Ala Leu Thr Leu
                85                  90                  95

Pro Ile Trp Ala Ala Lys Lys Asn Gly Trp Ile Phe Gly Thr Phe
                100                 105                 110

Leu Cys Lys Val Val Ser Leu Leu Lys Glu Val Asn Phe Tyr Ser Gly
            115                 120                 125

Ile Leu Leu Leu Ala Cys Ile Ser Val Asp Arg Tyr Leu Ala Ile Val
    130                 135                 140

His Ala Thr Arg Thr Leu Thr Gln Lys Arg Tyr Leu Val Lys Phe Val
145                 150                 155                 160

Cys Leu Ser Ile Trp Gly Leu Ser Leu Leu Ala Leu Pro Val Leu
                165                 170                 175

Leu Phe Arg Arg Thr Val Tyr Pro Thr Tyr Ile Ser Pro Val Cys Tyr
            180                 185                 190

Glu Asp Met Gly Asn Asn Thr Ala Lys Trp Arg Met Val Leu Arg Ile
        195                 200                 205

Leu Pro Gln Thr Phe Gly Phe Ile Leu Pro Leu Leu Ile Met Leu Phe
    210                 215                 220

Cys Tyr Gly Leu Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr His Leu Val Leu Leu Thr Asp Thr Leu Met
            260                 265                 270

Arg Thr Arg Leu Ile Lys Glu Thr Cys Gln Arg Arg Asn Asp Ile Asp
        275                 280                 285

Arg Ala Leu Asp Ala Thr Glu Ile Leu Gly Ile Leu His Ser Cys Leu
    290                 295                 300

Asn Pro Ile Ile Tyr Ala Phe Ile Gly Gln Lys Phe Arg His Gly Leu
305                 310                 315                 320

Leu Lys Ile Leu Ala Thr His Gly Leu Ile Ser Lys Asp Ser Leu Pro
                325                 330                 335

Lys Asp Ser Arg Pro Ser Phe Val Gly Ser Ser Ser Gly His Thr Ser
            340                 345                 350

Ser Thr Leu
        355

<210> SEQ ID NO 37
```

<211> LENGTH: 355
<212> TYPE: PRT
<213> ORGANISM: Papio hamadryas

<400> SEQUENCE: 37

```
Met Glu Ser Phe Asn Phe Glu Asp Phe Trp Thr Gly Glu Asp Phe Ser
1               5                   10                  15

Asn Tyr Ser Tyr Ser Ser Asp Leu Pro Pro Ser Leu Pro Asp Val Ala
            20                  25                  30

Pro Cys Arg Pro Glu Ser Leu Glu Ile Asn Lys Tyr Phe Val Val Ile
        35                  40                  45

Ile Tyr Val Leu Val Phe Leu Leu Ser Leu Leu Gly Asn Ser Leu Val
50                  55                  60

Met Leu Val Ile Leu His Ser Arg Val Gly Arg Ser Ile Thr Asp Val
65                  70                  75                  80

Tyr Leu Asn Leu Ala Met Ala Asp Leu Leu Phe Ala Leu Thr Leu
                85                  90                  95

Pro Ile Trp Ala Ala Ala Lys Val Asn Gly Trp Ile Phe Gly Thr Phe
            100                 105                 110

Leu Cys Lys Val Val Ser Leu Leu Lys Glu Val Asn Phe Tyr Ser Gly
        115                 120                 125

Ile Leu Leu Leu Ala Cys Ile Ser Val Asp Arg Tyr Leu Ala Ile Val
130                 135                 140

His Ala Thr Arg Thr Leu Ile Gln Lys Arg Tyr Leu Val Lys Phe Ile
145                 150                 155                 160

Cys Leu Ser Ile Trp Gly Leu Ser Leu Leu Leu Ala Leu Pro Val Leu
                165                 170                 175

Leu Phe Arg Arg Ala Val Tyr Pro Pro Tyr Ile Ser Pro Val Cys Tyr
            180                 185                 190

Glu Asp Met Gly Asn Asn Thr Ala Lys Trp Arg Met Val Leu Arg Ile
        195                 200                 205

Leu Pro Gln Thr Phe Gly Phe Ile Val Pro Leu Leu Ile Met Leu Phe
210                 215                 220

Cys Tyr Gly Leu Thr Leu Arg Thr Leu Phe Lys Ala His Met Gly Gln
225                 230                 235                 240

Lys His Arg Ala Met Arg Val Ile Phe Ala Val Val Leu Ile Phe Leu
                245                 250                 255

Leu Cys Trp Leu Pro Tyr His Leu Val Leu Leu Ala Asp Thr Leu Met
            260                 265                 270

Arg Thr Arg Leu Ile Asn Glu Thr Cys Gln Arg His Ser Asp Ile Asn
        275                 280                 285

Gln Ala Leu Asp Ala Thr Glu Ile Leu Gly Ile Phe His Ser Cys Leu
290                 295                 300

Asn Pro Leu Ile Tyr Ala Phe Ile Gly Gln Lys Phe Arg His Gly Leu
305                 310                 315                 320

Leu Lys Ile Leu Ala Thr His Gly Leu Ile Ser Lys Asp Ser Leu Pro
                325                 330                 335

Lys Asp Ser Arg Pro Ser Phe Val Gly Ser Ser Gly His Thr Ser
            340                 345                 350

Thr Thr Leu
        355
```

<210> SEQ ID NO 38
<211> LENGTH: 1068
<212> TYPE: DNA

<213> ORGANISM: Homo sapiens

<400> SEQUENCE: 38

```
atggagagtg acagctttga agatttctgg aaaggtgaag atcttagtaa ttacagttac      60
agctctaccc tgcccccttt tctactagat gccgccccat gtgaaccaga atccctggaa     120
atcaacaagt attttgtggt cattatctat gccctggtat tcctgctgag cctgctggga     180
aactccctcg tgatgctggt catcttatac agcagggtcg gccgctccgt cactgatgtc     240
tacctgctga acctagcctt ggccgaccta ctctttgccc tgaccttgcc catctgggcc     300
gcctccaagg tgaatggctg gattttggc acattcctgt gcaaggtggt ctcactcctg      360
aaggaagtca acttctatag tggcatcctg ctactggcct gcatcagtgt ggaccgttac     420
ctggccattg tccatgccac acgcacactg acccagaagc gctacttggt caaattcata     480
tgtctcagca tctggggtct gtccttgctc ctggccctgc tgtcttact tttccgaagg      540
accgtctact catccaatgt tagcccagcc tgctatgagg acatgggcaa caatacagca     600
aactggcgga tgctgttacg gatcctgccc cagtcctttg gcttcatcgt gccactgctg     660
atcatgctgt tctgctacgg attcacccctg cgtacgctgt ttaaggccca catggggcag    720
aagcaccggg ccatgcgggt catctttgct gtcgtcctca tcttcctgct ttgctggctg     780
ccctacaacc tggtcctgct ggcagacacc ctcatgagga cccaggtgat ccaggagacc     840
tgtgagcgcc gcaatcacat cgaccgggct ctggatgcca ccgagattct gggcatcctt     900
cacagctgcc tcaacccct catctacgcc ttcattggcc agaagtttcg ccatggactc      960
ctcaagattc tagctataca tggcttgatc agcaaggact ccctgcccaa agacagcagg    1020
ccttcctttg ttggctcttc ttcagggcac acttccacta ctctctaa                1068
```

<210> SEQ ID NO 39
<211> LENGTH: 1068
<212> TYPE: DNA
<213> ORGANISM: Pan troglodytes

<400> SEQUENCE: 39

```
atggagagtg acagctttga agatttctgg aaaggtgaag atcttagtaa ttacagttac      60
agctctaccc tgcccccttt tctactagat gccgccccat gtgaaccaga atccctggaa     120
atcaacaagt attttgtggt cattatctat gccctggtat tcctgctgag cctgctggga     180
aactccctcg tgatgctggt catcttatac agcagggtcg gccgctccgt cactgatgtc     240
tacctgctga acctagcctt ggccgaccta ctctttgccc tgaccttgcc catctgggcc     300
gcctccaagg tgaatggctg gattttggc acattcctgt gcaaggtggt ctcactcctg      360
aaggaagtca acttctatag tggcatcctg ctactggcct gcatcagtgt ggaccgttac     420
ctggccattg tccatgccac acgcacactg acccagaagc gctacttggt caaattcata     480
tgtctcagca tctggggtct gtccttgctc ctggccctgc tgtcttgct tttccgaagg      540
accgtctact catccaatgt tagcccagcc tgctatgagg acatgggcaa caatacagca     600
aactggcgga tgctgttacg gatcctgccc cagtcctttg gcttcatcgt gccgctgctg     660
atcatgctgt tctgctatgg attcacccctg cgtacattgt ttaaggccca catggggcag    720
aagcaccggg ccatgcgggt catctttgct gttgtcctca tcttcctgct ttgctggctg     780
ccctacaacc tggtcctgct ggcagacacc ctcatgagga cccaggtgat ccaggagacc     840
tgtgagcgcc gcaatcacat cgaccgggct ctggatgcca ccgagattct gggcatcctt     900
cacagctgcc tcaacccct catctacgcc ttcattggcc agaagtttcg ccatggactc      960
```

```
ctcaagattc tagctataca tggcttgatc agcaaggact ccctgcccaa agacagcagg      1020
ccttcctttg ttggctcttc ttcagggcac acttccacta ctctctaa                  1068

<210> SEQ ID NO 40
<211> LENGTH: 1053
<212> TYPE: DNA
<213> ORGANISM: Pan troglodytes

<400> SEQUENCE: 40
atggagagtg acagctttga agatttctgg aaaggtgaag atcttagtaa ttacagttac       60
agctctaccc tgcccccttt tctactagat gccgccccat gtgaaccaga atccctggaa      120
atcaacaagt attttgtggt cattatctat gccctggtat tcctgctgag cctgctggga      180
aactccctcg tgatgctggt catcttatac agcagggtcg gccgctccgt cactgatgtc      240
tacctgctga acctagcctt ggccgaccta ctctttgccc tgaccttgcc catctgggcc      300
gcctccaagg tgaatggctg gattttggc acattcctgt gcaaggtggt ctcactcctg       360
aaggaagtca acttctatag tggcatcctg ctactggcct gcatcagtgt ggaccgttac      420
ctggccattg tccatgccac acgcacactg acccagaagc gctacttggt caaattcata      480
tgtctcagca tctggggtct gtccttgctc ctggccctgc tgtcttgct tttccgaagg      540 accgtctact catccaatgt tagcccagcc tgctatgagg acatgggcaa caatacagca      600
aactggcgga tgctgttacg gatgctgccc cagtcctttg gcttcatcgt gccactgctg      660
atcatgctgt tctgctacgg attcaccctg cgtacattgt ttaaggccca catggggcag      720
aagcaccggg ccatgcgggt catctttgct gtcgtcctca tcttcctgct ttgctggctg      780
ccctacaacc tggtcctgct ggcagacacc ctcatgagga cccaggtgat ccaggagacc      840
tgtgagcgcc gcaatcacat caaccgggct ctggatgcca ccgagattct gggcatcctt      900
cacagctgcc tcaacccct catctacgcc ttcattgggc agaagtttcg ccatggactc      960
ctcaagattc tagccataca tggcttgatc agcaaggact ccctgcccaa agacagcagg     1020
ccttcctttg ttggctcttc ttcagggcac act                                  1053

<210> SEQ ID NO 41
<211> LENGTH: 1068
<212> TYPE: DNA
<213> ORGANISM: Gorilla gorilla

<400> SEQUENCE: 41
atggagagtg acagctttga agatttctgg aaaggtgaag atcttagtaa ttacagttac       60
agctctgact tgccccttt tctactagat gcctccccat gtgaaccaga atccctggaa       120
atcaacaagt attttgtggt cattatctat gccctggtat tcctgctgag cctgctggga      180
aactccctcg tgatactggt catcttatac agcagggtcg gccgctccgt cactgatgtc      240
tacctgctga acctggcctt ggccgaccta ctctttgccc tgaccttgcc catctgggcc      300
gcctccaagg tgaatggctg gattttggc acattcctgt gcaaggtggt ctcactcctg       360
aaggaagtca acttctatag tggcatcctg ctactggcct gcatcagtgt ggaccgttac      420
ctggccattg tccatgccac acgcacactg acccagaagc gctacttggt caagttcata      480
tgtctcagca tctggggtct gtccttgctc ctggccctgc tgtcttact tttccgaagg      540 accatctacc catccaatgt tagcccagtc tgctatgagg acatgggcaa caatacagca      600
aactggcgga tgctgttacg gatcctgccc cagtcctttg gcttcatcgt gccactgctg      660
```

-continued

```
atcatgctgt tctgctacgg attcaccctg cgtacactgt ttaaggccca catggggcag      720
aagcacaggg ccatgcgggt catctttgct gttgtcctca tcttcctgct ttgctggctg      780
ccctacaacc tggtcctgct ggcagacacc ctcatgagga cccaggtgat ccaggagacc      840
tgtgagcgcc gcaatcacat cgaccgggct ctggatgcca ccgagattct gggcatcctt      900
cacagctgcc tcaaccccct catctacgcc ttcattggcc agaagtttcg ccatggactc      960
ctcaagattc tagctataca tggcttgatc agcaaggact ccctgcccaa agacagcagg     1020
ccttcctttg ttggctcttc ttcagggcac acttccacta ctctctaa                  1068
```

<210> SEQ ID NO 42
<211> LENGTH: 1068
<212> TYPE: DNA
<213> ORGANISM: Gorilla gorilla

<400> SEQUENCE: 42

```
atggagagtg acagctttga agatttctgg aaaggtgaag atcttagtaa ttacagttac       60
agctctgact tgccccctttt tctactagat gcctcccat gtgaaccaga atccctggaa      120
atcaacaagt attttgtggt cattatctat gccctggtat tcctgctgag cctgctggga      180
aactccctcg tgatactggt catcttatac agcagggtcg gccgctccgt cactgatgtc      240
tacctgctga acctggcctt ggccgaccta ctctttgccc tgaccttgcc catctgggcc      300
gcctccaagg tgaatggctg attttttggc acattcctgt gcaaggtggt ctcactcctg      360
aaggaagtca acttctatag tggcatcctg ctactggcct gcatcagtgt ggaccgttac      420
ctggccattg tccatgccac acgcacactg acccagaagc gctacttggt caagttcata      480
tgtctcagca tctggggtct gtccttgctc tggccctgc ctgtcttact tttccgaagg      540
accatctacc catccaatgt tagcccagtc tgctatgagg acatgggcaa caatacagca      600
aactggcgga tgctgttacg gatcctgccc cagtcctttg gcttcatcgt gccactgctg      660
atcatgctgt tctgctacgg attcaccctg cgtacactgt ttaaggccca catggggcag      720
aagcacaggg ccatgcgggt catctttgct gttgtcctca tcttcctgct ttgctggctg      780
ccctacaacc tggtcctgct ggcagacacc ctcatgagga cccaggtgat ccaggagacc      840
tgtgagcgcc gcaatcacat caaccaggct ctggatgcca ccgagattct gggcatcctt      900
cacagctgcc tcaaccccct catctacgcc ttcattggcc agaagttttg ccatggactt      960
ctcaagattc tagctataca tggcttaatc agcaaggact ccctgcccaa agacagcagg     1020
ccttcctttg ttggctcttc ttcagggcac acttccacta ctctctaa                  1068
```

<210> SEQ ID NO 43
<211> LENGTH: 1068
<212> TYPE: DNA
<213> ORGANISM: Pongo pygmaeus
<220> FEATURE:
<223> OTHER INFORMATION: y can be T or C

<400> SEQUENCE: 43

```
atggagagtg acagctttga agatttcttg aaaggtgaag attttagtaa ttacagttac       60
agctctgacc tgccccctttt tctactagat gccgcccat gtgaaccaga atccctggaa      120
atcaacaagt attttgtggt cattatctat gtcctggtat tcctgctgag cctgctggga      180
aactccctcg tgatgctggt catcttatac agcagggtyg gccgctctgt cactgatgtc      240
tacctgctga acctggcctt ggccgaccta ctctttgccc tgaccttgcc catctgggcc      300
gcctccaagg tgactggctg attttttggc acattcctgt gcaaggtggt ctcactcctg      360
```

```
aaggaagtca acttctatag tggcatcctg ctactggcct gcatcagtgt ggaccgttac    420
ctggccattg tccatgccac acgcacactg acccagaagc gctacttggt caagttcata    480
tgtctcagca tctggggtct gtccttgctc ctggccctgc ctgtcttaat tttccgaaag    540
accatctacc caccctatgt tagcccagtc tgctatgagg acatgggcaa caatacagca    600
aactggcgga tgctgttacg gatcctgccc cagtcctttg gcttcatcgt gccgctgctg    660
atcatgctgt tctgctacgg attcaccctg cgtacgctgt ttaaggccca tatggggcag    720
aagcaccggg ccatgcgggt catctttgct gtcgtcctca tcttcctgct ttgctggctg    780
ccctacaacc tagtcctgct ggcagacacc ctcatgagga cctgggtgat ccaggagacc    840
tgtgagcgtc gcaatgacat cgaccgggct ctggaggcca ccgagattct gggcatcctt    900
cacagctgcc tcaacccect catctatgcc ttcattggcc agaagtttcg ccatggactc    960
ctcaagattc tagctataca tggcttgatc agcaaggact ccctgcccaa agacagcagg   1020
ccttcctttg ttggctcttc ttcagggcac acttccacta ctctctaa                1068
```

<210> SEQ ID NO 44
<211> LENGTH: 1068
<212> TYPE: DNA
<213> ORGANISM: Pongo pygmaeus

<400> SEQUENCE: 44

```
atggagagtg acagctttga agatttctgg aaaggtgaag accttagtaa ttacagttac     60
agctctaccc tgccccettt tctactagat gccgccccat gtgaaccaga atccctggaa    120
atcaacaagt attttgtggt cattatctat gtcctggtat tcctgctgag cctgctggga    180
aactccctcg tgatgctggt catcttatac agcagggttg gccgctctgt cactgatgtc    240
tacctgctga acctggcctt ggccgaccta ctctttgccc tgaccttgcc catctgggcc    300
gcctccaagg tgactggctg attttttggc acattcctgt gcaaggtggt ctcactcctg    360
aaggaagtca acttctatag tggcatcctg ctactggcct gcatcagtgt ggaccgttac    420
ctggccattg tccatgccac acgcacactg acccagaagc gctacttggt caaattcata    480
tgtctcagca tctggggtct gtccttgctc ctggccctgc ctgtcttaat tttccgaaag    540
accatctacc catcctatgt tagcccagcc tgctatgagg acatgggcaa caatacagca    600
aactggcgga tgctgttacg gatcctgccc cagtcctttg gcttcatcgt gccactgctg    660
atcatgctgt tctgctacgg attcaccctg cgtacgctgt ttaaggccca catggggcag    720
aagcacaggg ccatgcgggt catctttgct gtcgtcctca tcttcctgct ttgctggctg    780
ccctacaacc tggtcctgct ggcagacacc ctcatgagga accagatgat caatgagacc    840
tgtgagcgct gcaatcacat caaccaggcc ctggatgcca ccgagattct gggcatcctt    900
cacagctgcc tcaacccect catctacgcc ttcattggcc agaagtttcg ccatggactc    960
ctcaagattc tagttataca tggcttgatc agcaaggact ccctgcccaa agacagcagg   1020
ccttcctttg ttggctcttc ttcagggcac acttccacta ctctctaa                1068
```

<210> SEQ ID NO 45
<211> LENGTH: 1068
<212> TYPE: DNA
<213> ORGANISM: Macaca mulatta

<400> SEQUENCE: 45

```
atggagagtt caattttga agatctctgg aaaggtgaag attttagtaa ttacagttac      60
```

```
agctctgacc tgcccccttc tctaccagat gtcgccccat gtcgaccaga atccctggaa    120
atcaacaagt attttgtggt cattatctat gccctggtat tcctgctgag cttgctggga    180
aactccctcg tgatgctggt catcttacac agcagggtcg gccgctccat cactgatgtc    240
tacctactga acctggccat ggccgaccta ctgtttgccc tgaccttgcc catctgggct    300
gccgccaagg tgaatggctg attttttggc acattcctgt gcaaagtggt ctcactcctg    360
aaggaagtca acttctatag tggcatcctg ctactggcct gcatcagtgt ggaccgttac    420
ctggccattg tccatgccac acgcacactg acccagaagc gctacttggt caagttcgta    480
tgtctcagca tctggagtct atccttgctc ctggccctgc ctgtcttact tttccgaagg    540
actgtctacc tgacctatat tagcccagtc tgctatgagg acatgggcaa caatacagca    600
aaatggcgga tggtgttgcg gatcctgccc cagacctttg gcttcatctt gccgctgctg    660
atcatgctgt tctgctatgg attgaccctg cgcacgctgt ttaaggccca catggggcag    720
aagcaccggg ccatgcgggt catctttgct gtcgtcctca tcttcctact ctgctggctg    780
ccttaccacc tggtcctgct ggcagacacc ctcatgagga cccggttgat caacgagacc    840
tgtcagcgcc gcaacaacat cgaccaggcc ctggatgcca ccgagattct gggcatcctt    900
cacagctgcc tcaaccccct catctacgcc ttcattggcc agaagtttcg ccatggactc    960
ctcaagattc tagccacaca tggcttgatc agcaaggact ccctgcccaa agacagcagg    1020
ccttcctttg ttggctcttc ttcagggcac acttccacta ctctctga    1068

<210> SEQ ID NO 46
<211> LENGTH: 1068
<212> TYPE: DNA
<213> ORGANISM: Macaca mulatta

<400> SEQUENCE: 46
atggagagtg acagctttga agatctctgg aaaggtgaag attttagtaa ttacagttac    60
agctctgacc tgcccccttc tctaccagat gtcgccccat gtcgaccaga atccctggaa    120
atcaacaagt attttgtggt cattatctat gccctggtat tcctgctgag cttgctggga    180
aattctctcg tgatgctggt catcttatac agcagggtcg gccgctccgt cactgatgtc    240
tacctgctga acctagcctt ggccgaccta ctctttgccc tgaccttgcc catctgggcc    300
gccgccaagg tgaatggctg attttttggc acattcctgt gcaaggtggt ctcactcctg    360
aaggaagtca acttctatag tggcatcctg ctactggcct gcatcagtgt ggaccgttac    420
ctggccattg tccatgccac acgcacactg acccagaagc gctacttggt caaattcata    480
tgtctcagca tctggggtct gtccttgctc ctggccctgc ctgtcttact tttccgaagg    540
accgtctact catccaatgt tagcccagcc tgctatgagg acatgggcaa caatacagca    600
aactggcgga tgctgttacg gatcctgccc cagtcctttg gcttcatcgt gccactgctg    660
atcatgctgt tctgctacgg attcaccctg cgtacgctgt ttaaggccca catggggcag    720
aagcaccggg ccatgcgggt catctttgct gtcgtcctca tcttcctgct tgctggctg     780 ccctacagcc tggtcctgct ggcagacacc ctcatgagga cccaggtgat ccaggagacc    840
tgtgagcgcc gcaatcacat cgaccgggct ctggatgcca ccgagattct gggcatcctt    900
cacagctgcc tcaaccccct catctacgcc ttcattggcc agaagtttcg ccatggactc    960
ctcaagattc tagctataca tggcttgatc agcaaggact ccctgcccaa agacagcagg    1020
ccttcctttg ttggctcttc ttcagggcac acttccacta ctctctga    1068
```

<210> SEQ ID NO 47
<211> LENGTH: 1068
<212> TYPE: DNA
<213> ORGANISM: Cercopithecus pygerythrus

<400> SEQUENCE: 47

| | | | | | |
|---|---|---|---|---|---|
| atggagattt | ccaactttga | agatctctgg | aaaagtgaag | attttagtaa | ttacagttac | 60 |
| agctctgacc | tgccccttc | tctaccagat | gtcaccccat | gtcgaccaga | atccctggaa | 120 |
| atcaacaagt | attttgtggt | cattatctat | gccctggtat | tcctgctgag | cttgctggga | 180 |
| aactccctcg | tgatgctggt | catcttacac | agcagggtcg | gccgctccgt | cactgatgtc | 240 |
| tacctactga | acctggccat | ggccgaccta | ctgtttgccc | tgaccttgcc | catctgggct | 300 |
| gccgccaaga | agaatggctg | gattttggc | acattcctgt | gcaaggtggt | ctcactcctg | 360 |
| aaggaagtca | acttctacag | tggcatcctg | ctactggcct | gcatcagtgt | ggaccgttac | 420 |
| ctggccattg | tccatgccac | acgcacactg | acccagaagc | gctacttggt | caagttcgta | 480 |
| tgtctcagca | tctggggtct | gtccttactc | ctggccctgc | ccgtcttact | tttccgaagg | 540 |
| actgtctacc | cgacctatat | tagcccagtc | tgctatgagg | acatgggcaa | caatacagca | 600 |
| aaatggcgga | tggtgttgcg | gatcctgccc | cagaccttg | gcttcatctt | gccactgctg | 660 |
| atcatgctgt | tctgctatgg | attcaccttg | cgcacgctgt | ttaaggccca | catggggcag | 720 |
| aagcaccggg | ccatgcgggt | catctttgct | gttgtcctca | tcttcctact | ctgctggctg | 780 |
| ccctaccacc | tggtcctgct | gacagacact | ctcatgagga | cccggttgat | caaggagacc | 840 |
| tgtcaacgcc | gcaatgacat | cgaccgggcc | ctggatgcca | ccgagattct | gggcatcctt | 900 |
| cacagctgcc | tcaaccccat | catctacgcc | ttcattggcc | agaagttccg | ccatggactc | 960 |
| ctcaagattc | tagccacaca | tggcttgatc | agcaaggact | ccctgcccaa | agacagcagg | 1020 |
| ccttcctttg | ttggctcttc | ttcagggcac | acttccagta | ctctctga | | 1068 |

<210> SEQ ID NO 48
<211> LENGTH: 1068
<212> TYPE: DNA
<213> ORGANISM: Papio hamadryas
<220> FEATURE:
<223> OTHER INFORMATION: r can be G or A

<400> SEQUENCE: 48

| | | | | | |
|---|---|---|---|---|---|
| atggagagtt | tcaattttga | agatttctgg | acaggtgaag | attttagtaa | ttacagttac | 60 |
| agctctgacc | tgccccttc | tctaccagat | gtcgccccat | gtcgaccaga | atccctagaa | 120 |
| atcaacaagt | attttgtggt | cattatctat | gccctggtat | tcctgctgag | cttgctggga | 180 |
| aactccctcg | tgatgctggt | catcttacac | agcagggtcg | gccgctccat | cactgatgtc | 240 |
| tacctactga | acctggccat | ggccgaccta | ctgtttgccc | tgaccttgcc | catctgggct | 300 |
| gccgccaagg | tgaatggctg | gattttggc | acattcctgt | gcaaagtggt | ctcactcctg | 360 |
| aaggaagtca | acttctatag | tggcatcctg | ctactggcct | gcatcagtgt | ggaccgttac | 420 |
| ctggccattg | tccatgccac | acgcacactg | atccagaagc | gctacttggt | caagttcata | 480 |
| tgcctcagca | tctggggtct | gtccttgctc | ctggccctgc | ccgtcttact | tttccgaagg | 540 |
| gctgtctacc | crccctatat | tagcccagtc | tgctatgagg | acatgggcaa | caatacagca | 600 |
| aaatggcgga | tggtgttgcg | gatcctgccc | cagaccttg | gcttcatcgt | gccgctgctg | 660 |
| atcatgctgt | tctgctatgg | attcacccctg | cgcacgctgt | ttaaggccca | catggggcag | 720 |
| aagcaccggg | ccatgcgggt | catctttgct | gtcgtcctca | tcttcctact | ttgctggctg | 780 |

```
ccctaccacc tggtcctgct ggcagacacc ctcatgagga cccggttgat caacgagacc    840
tgtcagcgcc acagtgacat caaccaggcc ctggatgcca ccgagattct gggcatcttt    900
cacagctgcc tcaaccccct catctacgcc ttcattggcc agaagttccg ccatggactc    960
ctcaagattc tagccacaca tggcttgatc agcaaggact ccctgcccaa agacagcagg   1020
ccttcctttg ttggctcttc ttcaggacac acttccacta ctctctga                1068
```

```
<210> SEQ ID NO 49
<211> LENGTH: 24
<212> TYPE: DNA
<213> ORGANISM: Artificial sequence
<220> FEATURE:
<221> NAME/KEY: misc_feature
<223> OTHER INFORMATION: PCR primer corresponding to 5' UTR of human
      CXCR2

<400> SEQUENCE: 49
aggatttaag tttacctcaa aaat                                             24

<210> SEQ ID NO 50
<211> LENGTH: 23
<212> TYPE: DNA
<213> ORGANISM: Artificial sequence
<220> FEATURE:
<221> NAME/KEY: misc_feature
<223> OTHER INFORMATION: PCR primer corresponding to 3' UTR of human
      CXCR2

<400> SEQUENCE: 50
cggggctgca cttaggcagg agg                                              23

<210> SEQ ID NO 51
<211> LENGTH: 39
<212> TYPE: DNA
<213> ORGANISM: artificial sequence
<220> FEATURE:
<221> NAME/KEY: misc_feature
<223> OTHER INFORMATION: sense primer for PCR

<400> SEQUENCE: 51
acaggtaccg ccaccatgga gagtgacagc tttgaagat                             39

<210> SEQ ID NO 52
<211> LENGTH: 30
<212> TYPE: DNA
<213> ORGANISM: Artificial sequence
<220> FEATURE:
<221> NAME/KEY: misc_feature
<223> OTHER INFORMATION: antisense primer for PCR

<400> SEQUENCE: 52
gcgctcgagt tagagagtag tggaagtgtg                                       30

<210> SEQ ID NO 53
<211> LENGTH: 39
<212> TYPE: DNA
<213> ORGANISM: Artificial sequence
<220> FEATURE:
<221> NAME/KEY: misc_feature
<223> OTHER INFORMATION: sense primer for PCR

<400> SEQUENCE: 53
acaggtaccg ccaccatgga gagtgacagc tttgaagat                             39

<210> SEQ ID NO 54
```

<211> LENGTH: 30
<212> TYPE: DNA
<213> ORGANISM: Artificial sequence
<220> FEATURE:
<221> NAME/KEY: misc_feature
<223> OTHER INFORMATION: antisense primer for PCR

<400> SEQUENCE: 54
gcgctcgagt tagagagtag tggaagtgtg                              30

<210> SEQ ID NO 55
<211> LENGTH: 39
<212> TYPE: DNA
<213> ORGANISM: Artificial sequence
<220> FEATURE:
<221> NAME/KEY: misc_feature
<223> OTHER INFORMATION: sense primer for PCR

<400> SEQUENCE: 55
acaggtaccg ccaccatgga gagtgacagc tttgaagat                    39

<210> SEQ ID NO 56
<211> LENGTH: 30
<212> TYPE: DNA
<213> ORGANISM: Artificial sequence
<220> FEATURE:
<221> NAME/KEY: misc_feature
<223> OTHER INFORMATION: antisense primer for PCR

<400> SEQUENCE: 56
gcgctcgagt tagagagtag tggaagtgtg                              30

<210> SEQ ID NO 57
<211> LENGTH: 42
<212> TYPE: DNA
<213> ORGANISM: Artificial sequence
<220> FEATURE:
<221> NAME/KEY: misc_feature
<223> OTHER INFORMATION: sense primer for PCR

<400> SEQUENCE: 57
ataggtaccg ccaccatgga gagtttcaat tttgaagatc tc                42

<210> SEQ ID NO 58
<211> LENGTH: 30
<212> TYPE: DNA
<213> ORGANISM: Artificial sequence
<220> FEATURE:
<221> NAME/KEY: misc_feature
<223> OTHER INFORMATION: Artificial sequence

<400> SEQUENCE: 58
gcgctcgagt cagagagtag tggaagtgtg                              30

<210> SEQ ID NO 59
<211> LENGTH: 42
<212> TYPE: DNA
<213> ORGANISM: Artificial sequence
<220> FEATURE:
<221> NAME/KEY: misc_feature
<223> OTHER INFORMATION: sense primer for PCR

<400> SEQUENCE: 59
ataggtaccg ccaccatgga gatttccaac tttgaagatc tc                42

<210> SEQ ID NO 60
<211> LENGTH: 30

```
<212> TYPE: DNA
<213> ORGANISM: Artificial sequence
<220> FEATURE:
<221> NAME/KEY: misc_feature
<223> OTHER INFORMATION: antisense primer for PCR

<400> SEQUENCE: 60
gcgctcgagt cagagagtac tggaagtgtg                                    30

<210> SEQ ID NO 61
<211> LENGTH: 39
<212> TYPE: DNA
<213> ORGANISM: Artificial sequence
<220> FEATURE:
<221> NAME/KEY: misc_feature
<223> OTHER INFORMATION: sense primer for PCR

<400> SEQUENCE: 61
ataggtaccg ccaccatgga gagtttcaat tttgaagat                          39

<210> SEQ ID NO 62
<211> LENGTH: 30
<212> TYPE: DNA
<213> ORGANISM: Artificial sequence
<220> FEATURE:
<221> NAME/KEY: misc_feature
<223> OTHER INFORMATION: antisense primer for PCR

<400> SEQUENCE: 62
gcgctcgagt cagagagtag tggaagtgtg                                    30

<210> SEQ ID NO 63
<211> LENGTH: 24
<212> TYPE: DNA
<213> ORGANISM: Artificial sequence
<220> FEATURE:
<221> NAME/KEY: misc_feature
<223> OTHER INFORMATION: antisense primer for PCR

<400> SEQUENCE: 63
ggccgcctct tcaggaccaa ggtc                                          24
```

US 7,041,463 B2

ORTHOLOGUES OF HUMAN RECEPTORS AND METHODS OF USE

CROSS REFERENCE TO RELATED APPLICATION

This application is a continuation-in-part of U.S. patent application Ser. No. 09/576,160 now U.S. Pat. No. 6,469,150 filed May 22, 2000, the entire disclosure of which is hereby incorporated by reference into the subject application.

FIELD OF THE INVENTION

The invention relates to the use of orthologous polypeptides, for example, bradykinin $B_1$ and CXCR2 (IL-8RB) receptors, to identify suitable animal models for the testing of compounds with potential efficacy as receptor modulators and to identify compounds having dual specificity for receptors from different species. The invention also relates to recombinant expression vectors containing nucleotide sequences encoding bradykinin $B_1$ and CXCR2 receptors, recombinant host cells capable of expressing the receptors and methods for identifying modulators of bradykinin $B_1$ and CXCR2 receptor activity.

BACKGROUND OF THE INVENTION

In classical approaches to drug discovery, before the routine use of molecular biological methods, the activity of test and lead compounds were typically first analyzed by direct in vivo administration into animals to monitor a biological response, or alternatively, were tested in vitro using animal tissues. This drug discovery paradigm resulted in the identification of compounds with biological activity (efficacy) in the test animal but of unknown efficacy in humans. In some examples, efficacy in humans was weakly indicative of animal test systems that differ significantly from the human system. The result of such poorly predictive animal models was costly and time consuming.

In more recent paradigms of drug discovery, initial screening efforts are typically conducted in vitro on cloned human targets but additional secondary properties of lead candidates can then be complicated by lack of efficacy in in vivo animal models of choice. For example, the non-peptide substance P antagonist CP-96,345 showed high affinity ($IC_{50}$=0.4 nM) for cloned human neurokinin-1 (NK-1) receptor, but only 40 nM $IC_{50}$ at cloned rat NK1 receptor. Thus, compounds were much less efficacious in rat models than predicted. (Sachais et al. *Journal of Biological Chemistry*, Feb. 5, 1993 268(4):2319–2323; Fong et al. *Journal of Biological Chemistry*, Dec. 25, 1992 267(36):25668–25671.)

The problem of potent but highly species-specific compounds is being encountered with greater frequency as the use of cloned human receptors, enzymes, proteases, transporters and other gene products of interest to the drug discovery process, in high-throughput drug screening becomes standard procedure. An approach is needed that addresses this problem by (1) looking at in vitro predictors of in vivo efficacy in animals and (2) screening molecules potent at the human receptor for activity at various animal orthologues in order to identify dually active compounds, thus enabling one to predict, a priori, an animal model useful in early efficacy studies of potential drug candidates.

SUMMARY OF THE INVENTION

In one aspect, the invention relates to a method of identifying a compound with dual specificity to modulate the activity of a polypeptide of interest in two different species comprising contacting the compound with the polypeptide from a first species; measuring an effect of the compound on the activity of the first polypeptide; contacting the compound with the orthologous polypeptide from a second species; measuring an effect of the compound on the second polypeptide; and, based on these measurements, determining whether the compound is active at both polypeptides. In one embodiment, the method enables one to identify a compound having dual specificity to modulate the activity of a polypeptide of interest in a human and a non-human species.

In another aspect, the invention relates to a method of identifying a compound with dual specificity to modulate receptor activity in two different species comprising contacting the compound with a receptor from a first species; measuring an effect of the compound on the first receptor; contacting the compound with a receptor from a second species; measuring an effect of the compound on the second receptor; and, based on these measurements, determining whether the compound is active at both receptors. In one embodiment, the method enables one to identify a compound having dual specificity to modulate receptor activity in a human and a non-human species.

In another aspect, the invention relates to a method of identifying an animal model for testing compounds with potential efficacy as receptor modulators. The method comprises contacting a test compound with orthologous receptors from at least two species, one of which is human; measuring an effect of the compound on the receptors; and then selecting an animal model for further study of the compound's efficacy, wherein the animal selected represents a species having a receptor that exhibits the desired effect when contacted with the test compound.

In a related aspect, the invention relates to isolated nucleic acids comprising a nucleotide sequence encoding a bradykinin $B_1$ receptor amino acid sequence chosen from SEQ ID NO: 1, SEQ ID NO: 2, SEQ ID NO: 3, SEQ ID NO: 4, SEQ ID NO: 5 and SEQ ID NO: 6.

In another aspect, the invention relates to isolated nucleic acids comprising a bradykinin $B_1$ receptor nucleotide sequence chosen from SEQ ID NO: 7, SEQ ID NO: 8, SEQ ID NO: 9, SEQ ID NO: 10, SEQ ID NO: 11, and SEQ ID NO: 12.

In a related aspect, the invention relates to an expression vector which comprises a nucleotide sequence encoding a bradykinin $B_1$ receptor having a sequence chosen from SEQ ID NO: 1, SEQ ID NO: 2, SEQ ID NO: 3, SEQ ID NO: 4, SEQ ID NO: 5 and SEQ ID NO: 6 or a nucleotide sequence chosen from SEQ ID NO: 7, SEQ ID NO: 8, SEQ ID NO: 9, SEQ ID NO: 10, SEQ ID NO: 11 and SEQ ID NO: 12.

In yet another aspect, the invention relates to a recombinant cell comprising the expression vector described above and capable of expressing a bradykinin $B_1$ receptor from the expression vector, as well as a method for producing such a cell. The method comprises transfecting a suitable host cell with the expression vectors described above and maintaining the host cells under conditions in which the bradykinin $B_1$ receptor is expressed.

In a related aspect, the present invention relates to a method of identifying a compound that modulates bradykinin $B_1$ receptor activity. The method comprises contacting a test compound with a bradykinin $B_1$ receptor comprising an amino acid sequence chosen from SEQ ID NO: 1, SEQ ID NO: 2, SEQ ID NO: 3, SEQ ID NO: 4, SEQ ID NO: 5 and SEQ ID NO: 6 and measuring an effect of the compound on the receptor. The bradykinin $B_1$ receptor may be expressed by a recombinant host cell. The effect to be measured may be a binding effect, for example, the displacement of a peptidic or non-peptidic ligand or a native ligand, such as, des-Arg$^{10}$-kallidin, from the receptor.

In a related aspect, the invention relates to isolated nucleic acids comprising a nucleotide sequence encoding an CXCR2 receptor (CXCR2) amino acid sequence chosen from SEQ ID NO: 28, SEQ ID NO: 30, SEQ ID NO: 32, SEQ ID NO: 34, SEQ ID NO: 36 and SEQ ID NO: 37.

In another aspect, the invention relates to an nucleic acid comprising an CXCR2 nucleotide sequence chosen from SEQ ID NO: 39, SEQ ID NO: 41, SEQ ID NO: 43, SEQ ID NO: 45, SEQ ID NO: 47, and SEQ ID NO: 48.

In a related aspect, the invention relates to an expression vector which comprises a nucleotide sequence encoding an CXCR2 having a amino acid sequence chosen from SEQ ID NO: 28, SEQ ID NO: 30, SEQ ID NO: 32, SEQ ID NO: 34, SEQ ID NO: 36 and SEQ ID NO: 37, or a nucleotide sequence chosen from SEQ ID NO: 39, SEQ ID NO: 41, SEQ ID NO: 43, SEQ ID NO: 45, SEQ ID NO: 47, and SEQ ID NO: 48.

In yet another aspect, the invention relates to a recombinant cell comprising the expression vector described above and capable of expressing an CXCR2 from the expression vector, as well as a method for producing such a cell. The method comprises transfecting a suitable host cell with the expression vectors described above and maintaining the host cells under conditions in which the CXCR2 is expressed.

In a related aspect, the present invention relates to a method of identifying a compound that modulates CXCR2 activity. The method comprises contacting the test compound with an CXCR2 comprising an amino acid sequence chosen from SEQ ID NO: 1, SEQ ID NO: 2, SEQ ID NO: 3, SEQ ID NO: 4, SEQ ID NO: 5 and SEQ ID NO: 6 and measuring an effect of the compound on the receptor. The CXCR2 receptor may be expressed by a recombinant host cell. The effect to be measured may be a binding effect, for example, the displacement of a peptidic or non-peptidic ligand or a native ligand, such as, IL-8, from the receptor, or a functional effect.

BRIEF DESCRIPTION OF THE DRAWINGS

FIG. 3 shows the percent identity for all combinations of the cloned $B_1$ receptors.

FIGS. 7–12 show the competition binding curves and rank order of potencies at each of the cloned receptors.

FIG. 13 shows the $K_D$ and $K_I$ values at each of the different orthologues for four selected peptidic ligand and four non-peptidic small molecule antagonist compounds. The top portion of FIG. 13 shows the $K_D$ values for [$^3$H]-des-Arg$^{10}$-Kallidin at each of the cloned receptors. The bottom portion of FIG. 13 shows the $K_I$ values for the peptides and small molecules at the cloned receptors.

FIG. 16 shows the percent identity (upper triangle) and divergence (lower triangle) for all combinations of the cloned CXCR2 receptor DNA sequences.

FIG. 17 shows the percent identity (upper triangle) and divergence (lower triangle) for all combinations of the cloned CXCR2 receptor protein sequences.

DETAILED DESCRIPTION OF THE INVENTION

Figure 1:
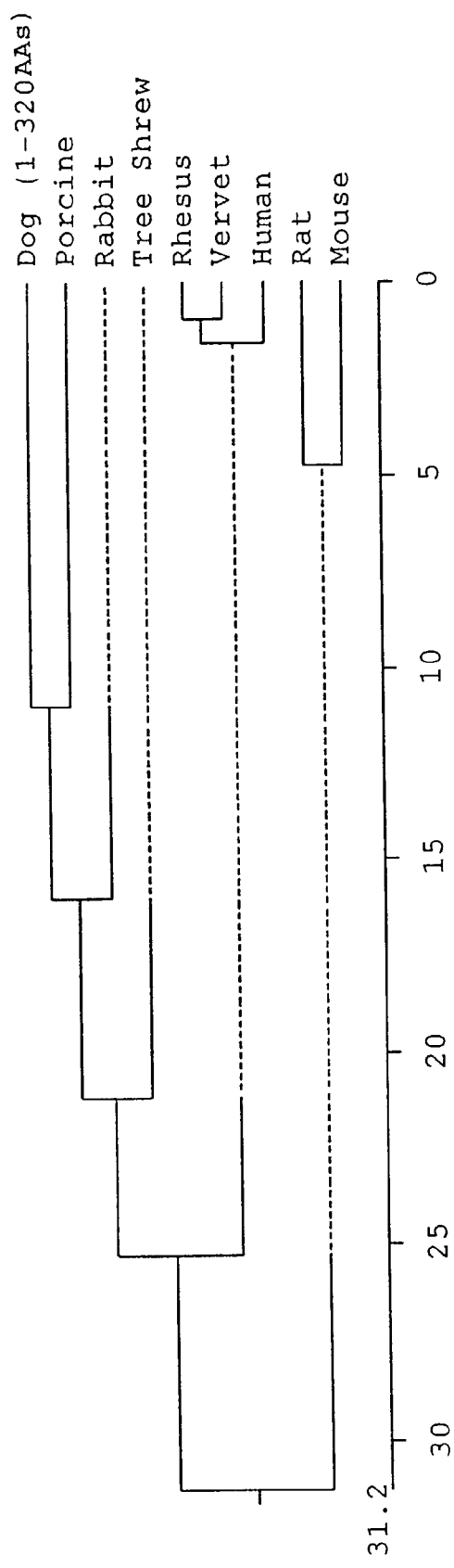
FIGS. 1 and 2 are schematics depicting putative phylogenetic relatedness of the $B_1$ receptor orthologues.

All patent applications, patents and literature references cited herein are hereby incorporated by reference in their entirety.

The invention encompasses bradykinin $B_1$ receptor nucleotides, bradykinin $B_1$ receptor proteins and peptides, CXCR2 receptor nucleotides, CXCR2 receptor proteins and peptides, as well as use of these molecules and other similar molecules to identify modulators of receptor activity. Modulators identified in this process, including but not limited to agonists, partial agonists, inverse agonists, antagonists, suppressors, inhibitors and inducers, may be useful as therapeutic agents in the treatment of pain and inflammation and other receptor related pathologies.

In practicing the present invention, many conventional techniques in molecular biology, microbiology, and recombinant DNA are used. Such techniques are well known and are explained in, for example, Sambrook et al., 2001, *Molecular Cloning: A Laboratory Manual*, Third Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984 (M. L. Gait ed.); Nucleic Acid Hybridization, 1985, (Hames and Higgins, eds.); *Transcription and Translation*, 1984 (Hames and Higgins, eds.); *Animal Cell Culture*, 1986 (R. I. Freshney ed.); *Immobilized Cells and Enzymes*, 1986, (IRL Press); Perbas, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); and *Methods in Enzymology* Vol. 154 and Vol. 155 (Wu and Grossman, and Wu, eds., respectively); *Current Protocols in Molecular Biology*, John Wiley & Sons, Inc. (1994), and all more current editions of these publications.

In the description that follows certain conventions will be followed as regards the usage of terminology.

The term "expression" refers to the transcription and translation of a structural gene (coding sequence) so that a protein (i.e. expression product) having the biological activity of a receptor is synthesized. It is understood that post-translational modifications may remove portions of the polypeptide which are not essential and that glycosylation and other post-translational modifications may also occur.

The term "transfection," as used herein, refers to the introduction of DNA into a host cell by any means, and includes, without limitation, transfection of episomes and other circular DNA forms. The expression vector may be introduced into host cells via any one of a number of techniques including but not limited to viral infection, transformation, transfection, lipofection, protoplast fusion, and electroporation.

The term "derivative(s)" refers to a protein, peptide, polypeptide or polynucleotide which is derived from one of the sequences described herein. It is intended to encompass polypeptides or peptides corresponding to functional domains (for example, one or more extracellular domains, one or more transmembrane domains, one or more cytoplasmic domains) of the receptor, a mutated, truncated or deleted receptor (that is, a receptor with one or more functional domains or portions thereof deleted), fusion proteins, and chimeras, such as the human/dog chimera disclosed herein and fragments thereof. The invention also encompasses nucleotide sequences encoding such products, as well as expression vectors containing these nucleotides and capable of producing such receptor products. A "functional derivative" is a polypeptide or polynucleotide which is derived from one of the sequences described herein and which retains the activity of the native molecule. Chimeric molecules, such as the canine/human chimera described below constitutes a "functional derivative."

Because the genetic code is degenerate, more than one codon may be used to encode a particular amino acid, and therefore, the amino acid sequence can be encoded by any set of similar DNA oligonucleotides. With respect to nucleotides, therefore, the term "derivative(s)" is also intended to encompass those DNA sequences which contain alternative codons which code for the eventual translation of the identical amino acid.

The term "dual specificity" is used to describe a ligand, either peptidic or non-peptidic, having potency at two different receptors within statistical variation of each other. A compound having dual specificity for two orthologous receptors will, generally, have an $IC_{50}$ or $K_1$ value within about 10- to 20-fold difference when done reproducibly under identical experimental conditions.

Nucleotides and Proteins

The bradykinin $B_1$ receptor genes from five mammalian species, namely, vervet monkey (SEQ ID NO. 7), rhesus macaque (SEQ ID NO. 8), tree shrew (SEQ ID NO. 9), pig (SEQ ID NO. 12), and dog (SEQ ID NO. 10), have been cloned and characterized. The deduced amino acid sequences for bradykinin $B_1$ receptors from vervet (SEQ ID NO. 1), rhesus (SEQ ID NO. 2), tree shrew (SEQ ID NO. 3), pig (SEQ ID NO. 6), and dog (SEQ ID NO. 4), are also disclosed herein. Additionally, the amino acid sequence for a dog/human chimeric receptor (SEQ ID NO. 5) and a nucleic acid sequence which encodes the chimera (SEQ ID NO. 11) are disclosed.

The bradykinin $B_1$ receptor polypeptides of the present invention include the polypeptides of SEQ ID NOs: 1–6; and a polypeptide comprising an amino acid sequence which has at least 80% identity to one of SEQ ID NOs: 1–6 over its entire length, and still more preferably at least 90% identity, and even still more preferably at least 95% identity to one of SEQ ID NOs: 1–6. Furthermore, those with at least 97–99% are highly preferred. Preferably, bradykinin $B_1$ receptor polypeptides exhibit at least one biological activity of the receptor.

The bradykinin $B_1$ receptor polypeptides may be in the form of the "mature" protein or may be a part of a larger protein such as a fusion protein. It is often advantageous to include an additional amino acid sequence which contains secretory or leader sequences, prosequences, sequences which aid in purification such as multiple histidine residues or other epitope tags, or an additional sequence for stability during recombinant production.

Additionally, the CXCR2 receptor nucleotide sequences from six primate species, namely, chimpanzee (SEQ ID NO. 13), gorilla (SEQ ID NO. 14), orangutan (SEQ ID NO. 15), rhesus macaque (SEQ ID NO. 16), vervet monkey (SEQ ID NO. 17), and baboon (SEQ ID NO. 18) have been cloned and characterized. The deduced amino acid sequences for CXCR2 receptors from chimpanzee (SEQ ID NO. 19), gorilla (SEQ ID NO. 20), orangutan (SEQ ID NO. 21), rhesus macaque (SEQ ID NO. 22), vervet monkey (SEQ ID NO. 23), and baboon (SEQ ID NO. 24), are also disclosed herein.

The invention also encompasses variant proteins that are functionally equivalent to the receptors encoded by the nucleotide sequences described above, as judged by any of a number of criteria, including but not limited to the ability to bind ligands known to interact with the receptor, the binding affinity for ligand, the resulting biological effect of ligand binding, for example, phosphatidyl inositol hydrolysis, release of intracellular $Ca^{++}$, or arachidonic acid release mediated by ligand binding and signal transduction molecules, such as diacyl glycerol and protein kinase C that cause a change in cellular metabolism, (e.g., ion flux, tyrosine phosphorylation).

Such functionally equivalent receptor proteins include but are not limited to those proteins containing additions, deletions or substitutions of amino acid residues within the amino acid sequence encoded by the receptor nucleotide sequences described, but which result in a silent change, thus producing a functionally equivalent gene product. Amino acid substitutions may be made on the basis of similarity in polarity, charge, solubility, size, hydrophobicity, hydrophilicity, and/or the amphipathic nature of the residues involved. For example, nonpolar (hydrophobic) neutral amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. While random mutations can be made to receptor DNA (using random mutagenesis techniques well known to those skilled in the art) and the resulting mutant receptor tested for activity, site-directed mutations of the receptor coding sequence can be engineered (using site-directed mutagenesis techniques well known to those skilled in the art) to generate mutant receptors with altered function, e.g., lower binding affinity for ligand and/or decreased signal transduction capacity.

Fragments of the receptor polypeptides are also included in the invention. A fragment is a polypeptide having an amino acid sequence that entirely is the same as part, but not all, of the amino acid sequence of the aforementioned receptor polypeptides. As with receptor polypeptides, fragments may be "free-standing," or comprised within a larger polypeptide of which they form a part or region, most preferably as a single continuous region.

Preferred fragments include, for example, truncation polypeptides having the amino acid sequence of receptor polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding regions, and high antigenic index regions. Other preferred fragments are biologically active fragments. Biologically active fragments are those that mediate or inhibit receptor activity, including those with a similar activity or an improved activity, or with a decreased undesirable activity. Also included are those fragments that are antigenic or immunogenic.

The receptor polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

The receptor polynucleotides of the present invention include isolated polynucleotides which encode the receptor polypeptides, and polynucleotides closely related thereto. More specifically, bradykinin $B_1$ receptor polynucleotides of the invention include polynucleotides comprising a nucleotide sequence selected from SEQ ID NOs: 7–12, encoding a bradykinin $B_1$ receptor polypeptide of SEQ ID NOs: 1–6. CXCR2 receptor polynucleotides of the invention include polynucleotides comprising a nucleotide sequence selected from SEQ ID NOs: 39, 41, 43, 45, 47 and 48, encoding an CXCR2 receptor polypeptide of SEQ ID Nos: 28, 30, 32, 34, 36 and 37. Receptor polynucleotides further include a polynucleotide comprising a nucleotide sequence that has at least 80% identity to a nucleotide sequence encoding one of the receptor polypeptides over its entire length, and a polynucleotide that is at least 80% identical to one of those set forth above over its entire length. In this regard, polynucleotides at least 90% identical are particularly preferred, and those with at least 95% identity are especially preferred. Furthermore, those with at least 97% identity are highly preferred and those with at least 98–99% identity are most highly preferred, with at least 99% identity being the most preferred. Also included are nucleotide sequences which have sufficient identity to a nucleotide sequence of the invention to hybridize under conditions useable for amplification or for use as a probe or marker. The invention also provides polynucleotides which are complementary to such receptor polynucleotides.

The nucleotide sequences encoding the receptor polypeptides of the present invention may be identical to the polypeptide-encoding sequences disclosed herein or may be any sequence, which as a result of the redundancy (degeneracy) of the genetic code, also encodes the polypeptides of the invention.

When the polynucleotides of the invention are used for the recombinant production of receptor polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding receptor variants comprising the amino acid sequence of a bradykinin $B_1$ receptor or CXCR2 receptor of the invention in which several, 5–10, 1–5, 1–3, 1–2 or 1 amino acid residues are substituted, deleted or added, in any combination. Nucleotide sequences which may be used as probes to identify the bradykinin $B_1$ receptors of the present invention are shown in SEQ ID NOs: 7–12 and encode the amino acid sequences of SEQ ID NOs: 1–6. Nucleotide sequences which may be used as probes to identify the CXCR2 receptor of the present invention are shown in SEQ ID Nos: 39, 41, 43, 45, 47 and 48 and encode the amino acid sequences of SEQ ID NOs: 28, 30, 32, 34, 36 and 37.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 90%, preferably at least 95%, and more preferably at least 97% identity between the sequences.

Polynucleotides of the invention, which are identical or sufficiently identical to a nucleotide sequence contained herein or a fragment thereof may be used as hybridization probes for cDNA and genomic DNA, to isolate full-length cDNAs and genomic clones encoding the receptor and to isolate cDNA and genomic clones of other genes that have a high sequence similarity to the receptor gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

The polynucleotides and polypeptides of the present invention may be employed as research reagents and materials for discovery of treatments and diagnostics to animal and human disease.

Isolation of DNA

DNA encoding a receptor, in accordance with the instant invention, may be obtained by chemical synthesis, by screening reverse transcripts of mRNA or cDNA from appropriate cells, for example, lung fibroblasts, aortic smooth muscle, mesangial cells, renal cells, intestinal smooth muscle cells, lymphoid cells or cell line cultures of the appropriate species or tissue, by screening genomic libraries, or by combinations of these procedures. Screening of mRNA, cDNA or genomic DNA may be carried out with oligonucleotide probes generated from the nucleic acid sequence information of the receptors disclosed herein.

For purposes of practicing the present invention, DNA encoding a receptor of a particular species can be obtained from any cDNA library prepared from tissue from the species believed to possess the receptor mRNA and to express it at a detectable level. The receptors can also be obtained from genomic libraries for the desired species.

Identification of receptor DNA is most conveniently accomplished by probing an appropriate cDNA or genomic library with labeled oligonucleotide sequences selected from known receptor sequences. For example, in one embodiment, a method for obtaining a polynucleotide encoding a receptor polypeptide comprises the steps of screening an appropriate library under stringent hybridization conditions with a labeled probe having a sequence selected from the nucleotide sequences described herein or a fragment thereof, and isolating full-length cDNA or genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C.

An alternative means to isolate the gene encoding a receptor is to use polymerase chain reaction (PCR) methodology as described in Sambrook et al., *Molecular Cloning: A Laboratory Manual*, third edition, Cold Spring Harbor Laboratory Press, Cold Spring Harbor, N.Y., 2001.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *Basic Methods In Molecular Biology* (1986) and Sambrook et al., *Molecular Cloning: A Laboratory Manual*, 2nd Ed., Cold Spring Harbor Laboratory Press, Cold Spring Harbor, N.Y. (1989). Such methods include calcium phosphate transfection, DEAE-dextran mediated transfection, microinjection, cationic lipid-mediated transfection, electroporation, transduction, scrape loading, ballistic introduction or infection.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, for example, those set forth in Sambrook et al., *Molecular Cloning, A Laboratory Manual* (supra).

Representative examples of appropriate hosts include bacterial cells, such as *E. coli*, Streptomyces and *Bacillus subtilis* cells; fungal cells, such as yeast cells and Aspergillus cells; insect cells such as Drosophila S2 and Spodoptera Sf9 cells; animal cells and plant cells. One of skill in the art will recognize that different host cells have characteristic and specific mechanisms for the post-translational processing and modification of proteins and gene products. Host cells suitable for expression of the inserted receptor sequences of the present invention are those having the capability to effect such post-translational modifications as necessary to produce a functional receptor. Suitable mammalian host cells include but are not limited to CHO, VERO, BHK, HeLa, COS, MDCK, HEK 293, 3T3, W138.

When using an episomally-based plasmid such as the pE3hyg episomal expression vector described herein, any eukaryotic cells which support stable replication of the plasmids may be used in practicing the invention. Non-limiting examples of host cells for use in the present invention include HEK 293 cells (American Type Culture Collection, Manassas, Va. (ATCC) Deposit Number CRL-1573), CV1EBNA cells (ATCC CRL10478), Hela cells, D98/Raji cells, 293EBNA (also referred to herein as "293E cells") available from Invitrogen, Cat. No. R62007, CV1 cells (ATCC Cat. No. CCL70) and 143B cells (ATCC Cat. No. CRL-8303).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the receptor polypeptide is to be expressed for use in screening assays, generally, it is preferred that the polypeptide be produced at the surface of the cell. In this event, the cells may be harvested prior to use in the screening assay. If receptor polypeptide is secreted into the medium, the medium can be recovered in order to recover and purify the polypeptide; if produced intracellularly, the cells must first be lysed before the polypeptide is recovered.

Receptor polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

The receptors of the present invention may be employed in a screening process for compounds which bind the receptor and which activate (agonists), partially activate (partial agonists, that is, compounds having intrinsic efficacy less than 100% and preferably less than 30%) or inhibit activation (antagonists and inverse agonists) of the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics.

Receptor polypeptides are responsible for many biological functions, including many pathologies. Accordingly, it is desirable to find compounds and drugs which stimulate the receptor on the one hand, or which can inhibit the function of the receptor on the other hand.

In general, such screening procedures involve producing appropriate cells which express a receptor polypeptide on the surface thereof. Such cells include cells from mammals, yeast, *Drosophila* or *E. coli*. Cells expressing the receptor (or cell membrane containing the expressed receptor) are then contacted with a test compound to observe binding, or stimulation or inhibition of a functional response.

One screening technique includes the use of cells which express receptor of this invention (for example, 293E cells stably transfected with an episome containing one of the polynucleotides of the invention) in a system which measures receptor binding, or extracellular pH or intracellular calcium changes caused by receptor activation. In this technique, compounds may be contacted with cells expressing the receptor polypeptide of the present invention. Receptor binding or a second messenger response, e.g., signal transduction, pH changes, or changes in calcium level, is then measured to determine whether the test compound activates or inhibits the receptor, or inhibits agonist-induced activation of the receptor.

Another method involves screening for receptor inhibitors/activators by determining inhibition or stimulation of receptor-mediated cAMP, inositol phosphate and/or calcium mobilization. Such a method involves transfecting a eukaryotic cell with the receptor of this invention to express the receptor on the cell surface. The cell bearing the receptor is then exposed to potential agonists, antagonists or inverse agonists in the presence and absence of ligand. The amount of cAMP or inositol phosphate accumulation is then measured. If a potential antagonist or inverse agonist binds the receptor, and thus inhibits receptor binding by native ligand or other agonist, the levels of receptor-mediated cAMP, inositol phosphate or calcium mobilization will be reduced. Conversely, if a potential agonist binds the receptor, thereby activating the receptor, the levels of receptor-mediated cAMP, inositol phosphate or calcium mobilization are increased.

The assays may simply test binding of a candidate compound wherein adherence to the receptor, or to cells bearing the receptor, is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed. Standard methods for conducting such screening assays are well understood in the art.

Examples of potential receptor inhibitors include antagonists, inverse agonists, weak partial agonists, antibodies or, in some cases, oligonucleotides or proteins which are closely related to the ligand of the receptor, e.g., peptides or small molecules which bind to the receptor but do not elicit a response, so that the activity of the receptor is prevented.

As discussed earlier, in more recent paradigms of drug discovery, in vitro screening efforts are typically conducted on cloned human targets but resulting properties of lead candidates are sometimes complicated by lack of efficacy in in vivo animal models of choice. Identification of the nucleotides and proteins of the present invention provide a unique opportunity for identifying an animal model for testing compounds, in vivo, which have potential efficacy as receptor modulators. The method comprises contacting the test compound with a receptors from at least two species; measuring an effect of the compound such as receptor binding or a second messenger response on the receptors; and finally, selecting an animal model wherein the animal chosen represents a species having a receptor that exhibits the desired effect when contacted with the test compound. In one embodiment, one of the species is a human and the other is a non-human.

EXAMPLES

Amino acid and nucleotide sequences were determined as described below. Clustal sequence alignments were performed using Megalign 4.01 from DNASTAR, Inc. (Madison, Wis.). Amino acid sequence alignments, phylogenetic relationships and pairwise comparison of amino acid identities were performed using Lasergene software (DNAStar, Inc. Madison, Wis.).

Example 1

$B_1$ Orthologues from Five Mammalian Species

Tree shrew (*Tupaia minor*) genomic DNA was obtained from Dr. Marc Allard (Dept. Of Biological Sciences, George Washington University, Washington, D.C.) Dog, pig, rabbit, human and rat genomic DNAs were purchased from Clonetech (Palo Alto, Calif.). Genomic DNA from Vervet monkey (*Cercopithecus pygerythrus*) was isolated from a liver biopsy specimen obtained from Caribbean Primates Ltd. (St. Kitts, West Indies). Genomic DNA from rhesus macaque (Macaca mulatta) was purchased from Clonetech (Palo Alto, Calif.).

Oligonucleotides to amplify the coding regions for the $B_1$ homologue from the human, rabbit and rat were designed according to published sequences and contain appropriate Kozak consensus sequences for subsequent expression (Table 1).

TABLE 1

Oligonucleotides used for isolation of B1 gene

| | | | Seq. ID No. |
|---|---|---|---|
| Uni- | sense | tgtycmkkycrrgtcactgtgsatggc | 13 |
| versal | antisense | gctgytttaattccgccagaa | 14 |
| Human | sense | ggactagtaccaccatggcatcatcctggc | 15 |
| | antisense | gcgtcgacggttcaatgctgttttaattccgcc | 16 |
| Rabbit | sense | gcatgccaccatggcgtccgaggtcttgttg | 17 |
| | antisense | tgacttataaagtccccagaaccctg | 18 |
| Rat | sense | gcatgccaccatggcgtccgaggtcttgttg | 17 |
| | antisense | tgacttataaagtccccagaaccctg | 18 |
| Ma- | sense | ataggtaccgccaccatggcatcctggccccctctagag | 19 |
| caque | antisense | gcgctcgaggctgttttaattccgccagaa | 20 |
| Vervet | sense | ataggtaccgccaccatggcatcctggccccctctagag | 19 |
| | antisense | gcgctcgaggctgttttaattccgccagaa | 20 |
| Tree | sense | ataggtaccgccaccatggcagcccagacactcctg | 21 |
| shrew | antisense | gcgctcgagttaattccgccagaaamgcc | 22 |
| Pig | sense | ataggtaccgccaccatggcctcccagaccctcgtg | 23 |
| | antisense | gcgctcgaggctgttttaattccgccagaa | 24 |
| Dog | sense | ataggtaccgccaccatggcatcgcgggcccccctg | 25 |
| | antisense | raccytggtcytrargagccggcc | 26 |

Polymerase chain reaction (PCR) was used to amplify the coding sequences from vervet monkey (*Cercopithecus pygerythrus*), rhesus macaque (*Macaca mulatta*), pig, and tree shrew (*Tupaia minor*). Degenerate oligonucleotides were designed to the consensus derived from human, rodent and lapine sequences from nt −24 to nt +5 (universal sense oligonucleotide, Table 1) and to the region across or near the stop codon (antisense). The resulting PCR amplicons were sequenced directly. Explicit oligos based on the PCR amplicon sequences were used to re-amplify from corresponding genomic DNAs. PCR products were digested with Kpn I and Xho I, and cloned into the corresponding sites of the episomal expression vector pE3hyg (Horlick et al., Gene 243(1–2) pp. 187–194, 2000).

Additionally, a canine/human chimeric bradykinin $B_1$ receptor comprising amino acids 1 to 320 of the canine sequence and amino acids 319–353 of human bradykinin $B_1$ receptor was generated. Any number of chimeric molecules, for example, a chimera comprising amino acids 1–315 of the canine sequence and amino acids 314–353 of the human sequence can be used.

For the canine/human chimera, a 150 bp fragment corresponding to human $B_1$ amino acids 319 to 354 was PCR amplified with the sense oligo, 5'-GGCCGGCTCTTCAG-GACCAAGGTC-3' (SEQ ID NO. 63) and the antisense oligo used for Rhesus, 5'-GCGCTCGAGGCTGTTTTAAT-TCCGCCAGAA-3' (SEQ. ID. NO. 20). The coding region for the first 320 codons of canine $B_1$ was successfully PCR amplified using the degenerate universal and dog antisense oligos (Table 1). Sequence information from this amplicon was used to make an explicit dog sense oligo (Table 1). PCR of the dog genomic DNA with this oligo and the original degenerate antisense oligo, raccytggtcytrargagccggcc (SEQ. ID. NO. 22), resulted in a fragment of 960 bp. The 960 bp partial dog $B_1$ PCR product and the 150 bp human $B_1$ PCR product were combined as the template for a second round of PCR amplification. The dog sense and the rhesus antisense oligos were used to create a chimera in this second round of PCR. The resulting 1.1 Kb PCR product was cleaved with KpnI and XhoI, and then cloned into the corresponding sites of the pE3-Hyg vector as described below.

It has been shown previously that the carboxy terminal cytoplasmic domain does not appear to play a role in the ligand binding properties of the human B1 receptor and therefore, the chimeric canine/human receptor described above was used in the experiments described below.

Host cells, 293-EBNA (293E)(Invitrogen, Carlsbad, Calif.) were transfected as follows with an episomal vector containing a bradykinin $B_1$ receptor nucleotide to be expressed. 293E cells were grown in Dulbecco's Modified Eagles Medium (DMEM) (Life Technologies, Gaithersburg, Md.) supplemented with 10% fetal bovine serum, 5 mM Glutamax II (Life Technologies, Gaithersburg, Md.), 100U/ml penicillin, and 100 µg/ml of streptomycin. The cells were plated in T75 flasks at a density of $2\times10^6$ cells/ml in growth media and incubated overnight. Transfection of the cells was by the calcium precipitation method (Sambrook et al. in Molecular Cloning: A Laboratory Manual, 2nd edition) using a total of 5 µg of DNA. The precipitate was added to the cells and then incubated for 6–18 hours. Following this incubation the cells were washed once with growth media (about 5 ml) and then fresh media was added (about 10 ml) and the cells incubated for an additional 24 hours. The cells were then sub-cultured 1:10 in selection media, growth media supplemented with an antibiotic to which the successfully transfected cell has acquired resistance.

Membrane Preparation

Membrane preparations for use in accordance with the methods of the present invention were generated as follows. 293E cells expressing $B_1$ receptors were harvested and pelleted. Cells were washed once with PBS and once with a membrane buffer (for example, 10 mM HEPES pH 7.5, 1 µM phosphoramidon, 3 µM amastatin, 1 µM captopril, 2 µM dithiothreitol (DTT)). Cells were resuspended in membrane buffer and Dounce homogenized on ice 35 times. The membranes were collected by centrifugation at 15,000×g for 30 min. at 4° C. and resuspended in membrane buffer containing 0.2% bovine serum albumin (BSA) at a final concentration of approximately $5\times10^7$ cell equivalents per ml. Aliquots were flash frozen and stored at –80° C. Frozen aliquots were subsequently thawed, diluted, and sonicated on ice using a Branson Sonifier® 250 (4×5 sec, 40% output).

Prior to use in a binding assay, a membrane preparation is "calibrated" as described below to determine the amount of membrane preparation to be used. A frozen sample of a membrane preparation is thawed and the preparation diluted in assay buffer to obtain several different concentrations of membranes, for example, 1:5, 1:10, 1:20, 1:40 and so on. The diluted membrane preparation is sonicated in a bath style sonicator for 15 seconds at room temperature. Each dilution is plated in a 96-well plate, for example, with quintuplicate samples for binding of ligand and wells to evaluate non-specific binding in triplicate. The dilutions that yield approximately 200 cpm total counts are chosen for subsequent assays.

Binding Assays

The method of the present invention employs a binding assay such as the one described below. A suitable binding assay buffer for rat receptor binding consists of 10 mM TES pH 6.8, 1 mM EDTA, 1 µM Plummer's Inhibitor, 1 µM enalapril, and 10 µM thiorphan. The buffer for all other species consists of Hank's Buffered Saline Solution (HBSS), 10 mM HEPES pH 7.5, 1 mM 1,10-phenanthroline, and 140 mg/L bacitracin. Competitor compounds, peptide or small molecule, were resuspended in 100% dimethyl sulfoxide (DMSO) and diluted to a final concentration of 5% DMSO in the reaction mixture. Binding reactions were carried out in 96-well microtiter dishes, 100 µl reaction volume per well in the presence of 1.5 nM (rat) or 0.6 nM (all other species) $[^3H]$-des-Arg$^{10}$-kallidin ($[^3H]$-dAKd) (NEN, Boston, Mass.). Binding reactions were initially chilled on ice for 10 min. and then continued at 4° C. for 1 hour. Reaction mixtures were transferred to glass fiber filter-plates which had been pre-blocked with 0.3% polyethyleneimine (PEI) (Sigma, St. Louis, Mo.), and washed 6 times with ice cold 50 mM Tris pH 7.5. 50 µl of scintillation fluid was added to each well and plates were counted in a Wallac Microbeta® TriLux for 10 min. per well.

Figure 2:
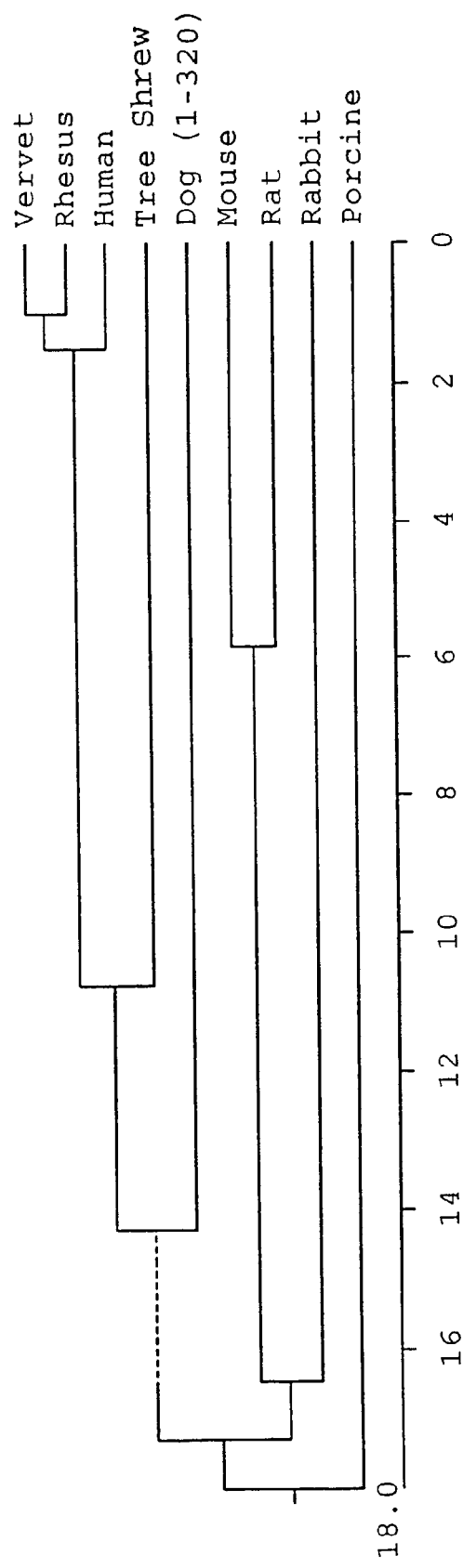

In order to assess the species-specificity profiles of potential small molecule antagonist molecules, the $B_1$ receptor coding regions from 5 mammalian species were cloned and characterized. Because the coding sequence for the $B_1$ gene is known to be contained within a single exon, the relevant sequences were obtained by performing PCR directly on genomic DNA obtained from each species. A pairwise comparison of percent amino acid identity among the $B_1$ receptor orthologues (shown in FIG. 3) reveals that the sequences of the $B_1$ receptor orthologues appear to be somewhat less well evolutionarily conserved than many other G protein coupled receptors (GPCRs) and numerous amino acid changes are found scattered throughout the receptor sequences. A dendritic chart showing a putative evolutionary relationship among the sequences (FIGS. 1 and 2) is consistent with current concepts and demonstrates that both primates are very closely related to the human sequence (96% identical). The next most closely related sequence to humans belongs to the tree shrew (80.5% identical). Tree shrews are mouse-to-rat sized animals in the order Scandentia, and have been postulated to be among the closest relative to primates. Next in order of amino acid identity is the rabbit orthologue (77.1%), followed by dog (75.3%). Murine and porcine sequences show even less conservation.

Pharmacology of Peptidic Ligands at the $B_1$ Receptors

The pharmacological profile of the $B_1$ orthologues was assessed using four $B_1$ and $B_2$ peptidic ligands (FIGS. 7–12).

The average dissociation constant ($K_D$) of dAkd appears to be of mostly the same magnitude at each of the animal orthologues, varying between 0.6 nM (human) and 1.3 nM (rabbit) to 4.2 nM (tree shrew) (FIG. 13). The measured affinities are within the range of values reported in the literature for human and rabbit $B_1$ receptors. Inhibition constants ($K_1$) were calculated from $IC_{50}$ values generated by the four peptide ligands, dAKd, BK, [des-Arg$^{10}$] [Leu$^9$] kallidin (dALKd), and [des-Arg$^9$]BK (dABK) in the presence of 0.6 nM or 1.5 nM [$^3$H]-dAKd, as indicated in the materials and methods section above. These results are shown in FIG. 13. Whereas BK is inactive and dAKd is approximately equipotent at all of the species homologues, the other two peptidic ligands exhibit significant differences in affinity among the various $B_1$ receptors. For example, dALKd is more than an order of magnitude weaker at the dog $B_1$ vs. the other $B_1$ receptors; dABk exhibits low nM potency at dog, inactivity at human, tree shrew and rhesus macaque, and weak activity at rabbit and pig B1.

Pharmacology of Non-Peptidic Ligands at the $B_1$ Receptors.

Figure 4:
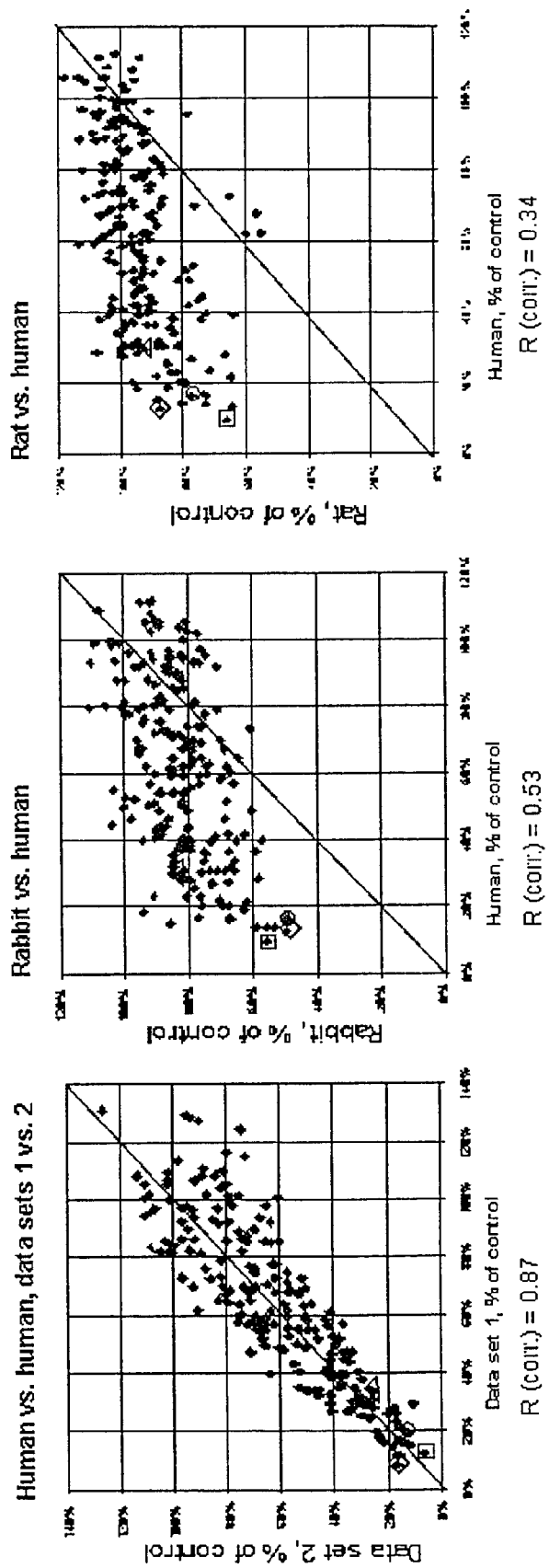
FIGS. 4–6 show the results of comparison of activity of selected test compounds at animal vs. human $B_1$ receptor orthologues.
Figure 5:
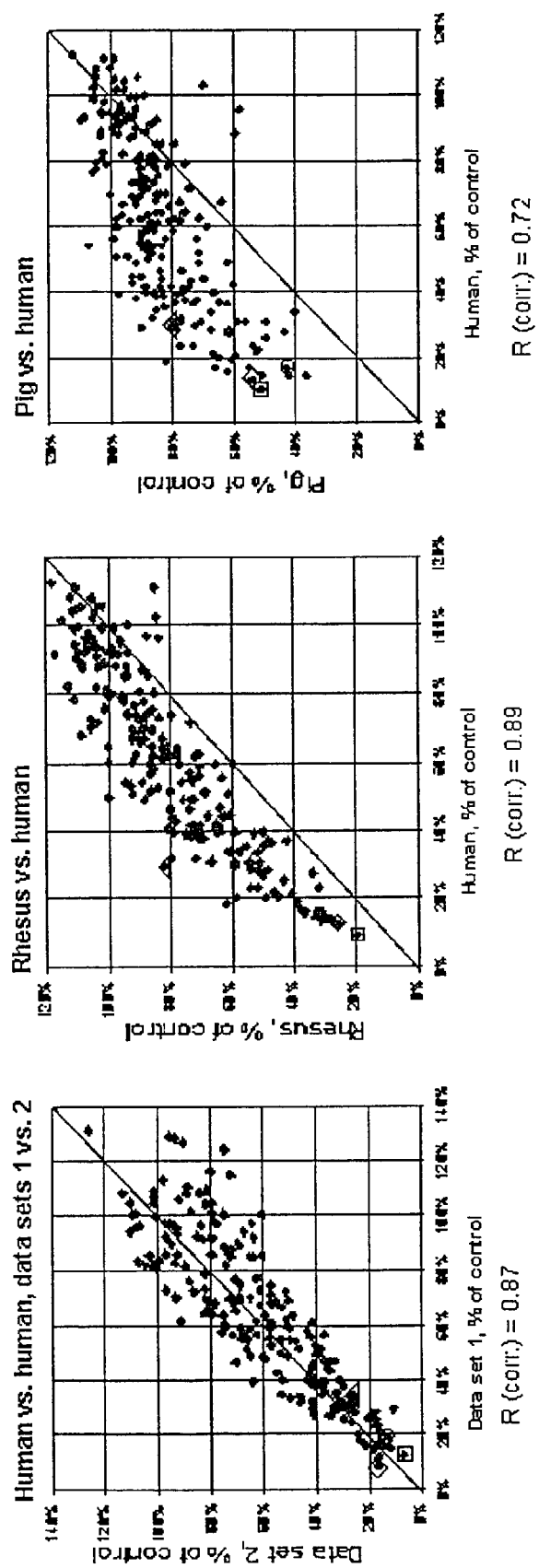
Figure 6:
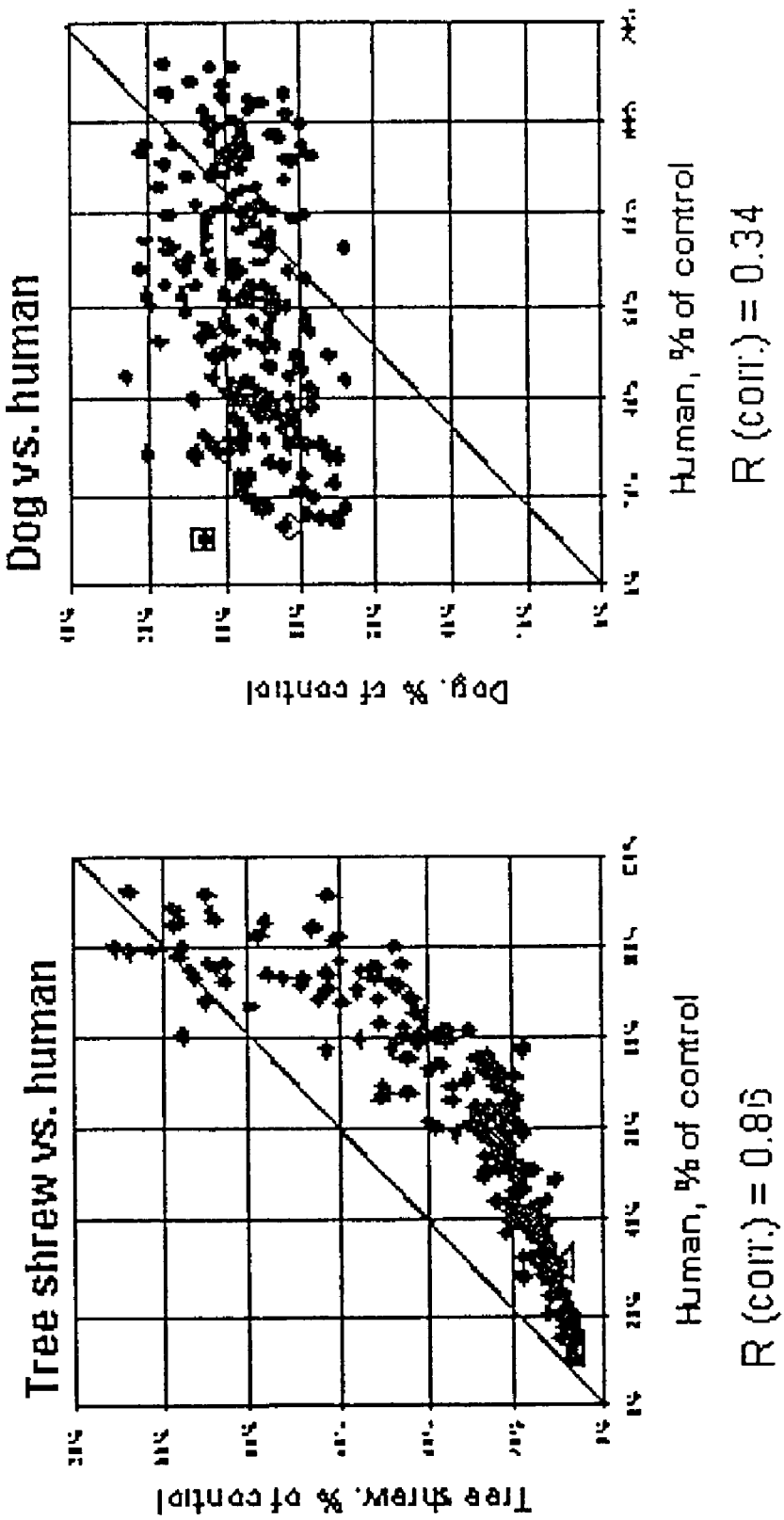

A subset of compounds that retain significant potency at most of the receptors was identified. Comparison of the activity of the compounds at animal vs. human $B_1$ receptor orthologues is shown in the scattergrams of FIGS. 4–6. The solid line at 45° in each panel represents an isocline of equal potency. FIGS. 4–6 show two independent human data sets compared to each other, and species-to-human comparisons, as labeled at the top of each scattergram. The correlation coefficients of each pair of data sets is shown below each figure. Compounds were tested at 1 µM concentration at the rat $B_1$ receptor, and at 0.1 µM concentration at all other animal orthologues. Displacement was tested in the presence of 1.5 nM [$^3$H]-dAKd for rat $B_1$, and 0.6 nM for all other $B_1$ receptors. Data points are marked as follow: □, PS978163; ◇, PS596668; ○, PS972282; △, PS309799. Conversely, a subset of compounds that exhibit considerable differences in specificity among the orthologues was also identified (data point for PS309799 shown enclosed by triangle). To verify the validity of the scattergram results, the potencies of these four non-peptide compounds were further assessed by ligand displacement assays at the $B_1$ orthologous receptors. A comparison of $K_1$s among the four compounds revealed dramatic differences in species specificity. Compound PS309799 showed the greatest variation of activity, ranging from low nM potency in tree shrew and human to inactive at dog and rabbit. PS596668 had a similar activity profile to PS309799 except it demonstrated potent activity at the rabbit B1. The remaining two compounds, PS972282 and PS978163, had measurable affinity constants at all six species, although PS978163 was considerably weaker at pig and dog.

Figure 9:
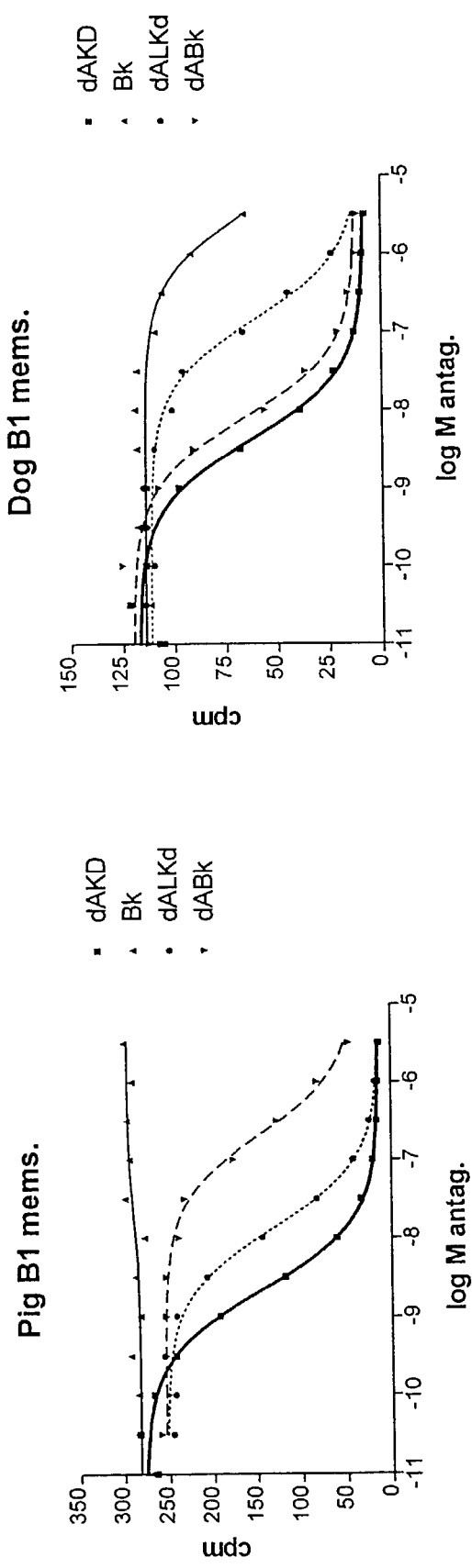
Figure 10:
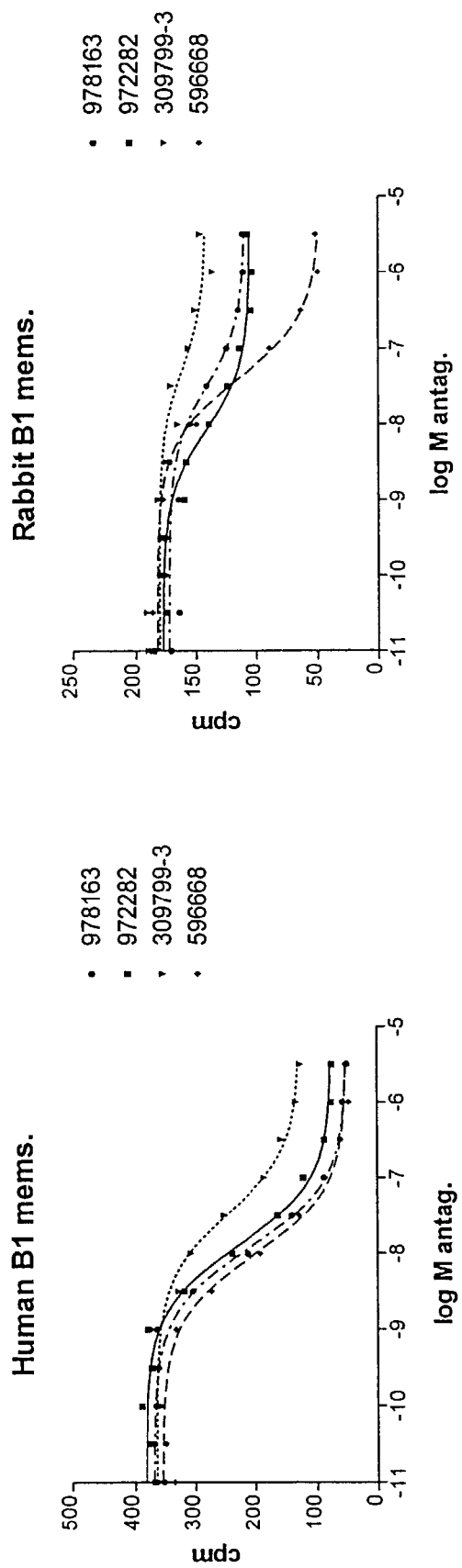
Figure 12:
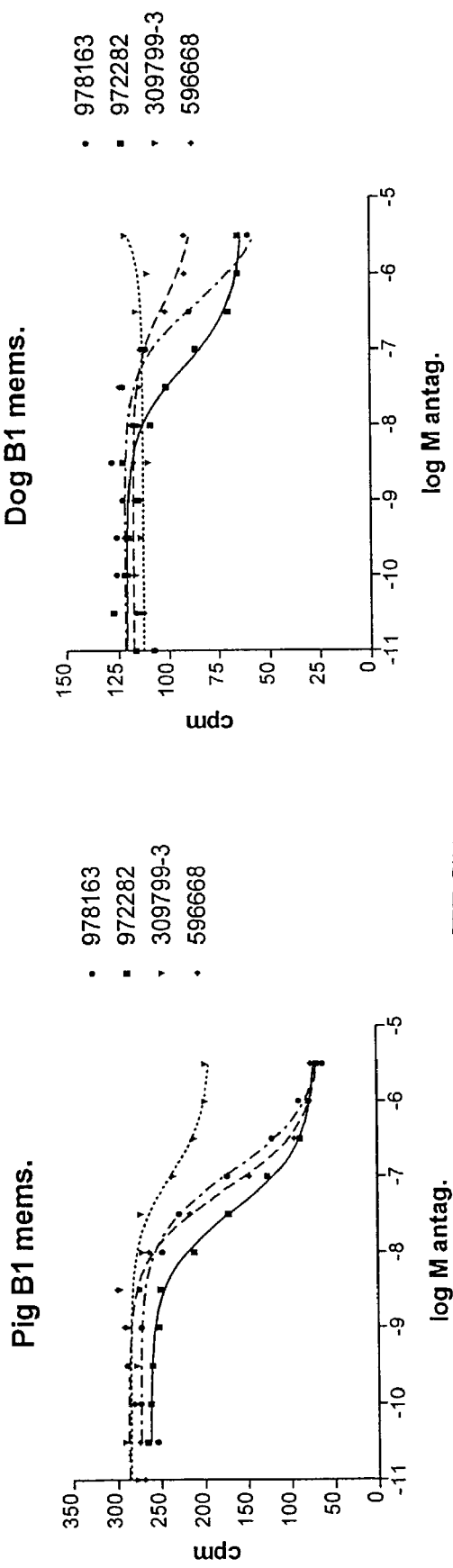

FIGS. 7–12 show the competition binding curves at each of the cloned receptors. In FIGS. 7–9, the binding of four peptides are shown, des-Arg$^{10}$-Kallidin [dAKd], Bradykinin [Bk], des-Arg$^{10}$-Leu$^9$-Kallidin [dALKd], and des-Arg$^9$-Bradykinin [dABk]. All of these receptors have strong affinity for $dAK_D$ but not BK and are, therefore, subtype 1 receptors. The potencies of the four peptides do vary at the different orthologues, however. FIGS. 10–12 shows competition with four small molecules that have been identified. These also show various levels of activity at the different receptors.

Example 2

CXCR2 Orthologues from Six Mammalian Species

DNAs encoding interleukin 8 receptor B (IL8RB/CXCR2) from six primate species were also cloned and characterized and the DNAs were expressed in recombinant host cells, which produce active recombinant protein. The encoded receptors are capable of binding interleukin 8, Gro-alpha and ENA-78. In addition, the recombinant host cells are utilized to establish a method for identifying modulators of receptor activity, and receptor modulators are identified. The cDNAs encoding these specific receptors can also be used to define compounds that will interact with the human receptor and to identify compounds of therapeutic value in the treatment of inflammation.

Chimpanzee (*Pan troglodytes*), gorilla (*Gorilla gorilla*), and orangutan (*Pongo pygmaeus*) genomic DNAs were isolated from lymphoblast cells (European Collection of Cell Culture, Centre for Applied Microbiology and Research, ECACC/CAMR, Accession Numbers: 89072704, 89072703, and 89072705, respectively). Rhesus macaque (*Macaca mulatta*) genomic DNA was purchased from Clonetec (Palo Alto, Calif.). Vervet (*Cercopithecus pygerythrus*) genomic DNA was isolated from a liver biopsy specimen obtained from Dr. Frank Ervin, Caribbean Primates Ltd.). Baboon (*Papio hamadryas*) genomic DNA was isolated from lymphoblast cells (American Tissue Culture Collection, CRL-1495).

Polymerase chain reaction (PCR) was used to amplify the coding sequences from chimpanzee (*Pan troglodytes*), gorilla (*Gorilla gorilla*), orangutan (*Pongo pygmaeus*), rhesus macaque (*Macaca mulatta*), vervet monkey (*Cercopithecus pygerythrus*), and baboon (*Papio hamadryas*). Sense (5-AGGATTTAAGTTTACCTCAAAAAT-3') (SEQ ID NO: 49) and antisense (5'-CGGGGCTGCACTTAGGCAGGAGG-3) (SEQ ID NO: 50) oligonucleotidess corresponding to the 5'-UTR and 3'-UTR of the human IL8RB were used to PCR all six primate IL8RB orthologue sequences from genomic DNA. The resulting PCR amplicons were sequenced directly. Explicit oligonucleotides (Table 2) based on the PCR amplicon sequences were used to re-amplify from corresponding genomic DNAs. The 5'-oligonucleotide also included a Kpn I restriction site and consensus Kozak sequence (5'-GCCACC-3') immediately upstream of the start codon. The 3'-oligo included a Xho I restriction site. The PCR products were cleaved with Kpn I and Xho I, and cloned into the corresponding sites of the episomal expression vector pE3-Hygromycin (Horlick et al., Gene 243(1–2) pp. 187–194, 2000).

These expression vectors were stably transfected into human embryonic kidney cells harboring Epstein Barr virus E1 gene (293E cells from Invitrogen) using calcium phosphate precipitation method. Stable cell lines were selected in the presence of hygromycin B.

TABLE 2

Oligonucleotides used for isolation of CXCR2 nucleotides

|  |  |  | Seq. ID No. |
|---|---|---|---|
| chimpanzee | sense | acaggtaccgccaccatggagagtgacagctttgaagat | 51 |
| | antisense | gcgctcgagttagagagtagtggaagtgtg | 52 |
| gorilla | sense | acaggtaccgccaccatggagagtgacagctttgaagat | 53 |
| | antisense | gcgctcgagttagagagtagtggaagtgtg | 54 |

TABLE 2-continued

Oligonucleotides used for isolation of CXCR2 nucleotides

| | | | Seq. ID No. |
|---|---|---|---|
| orangutan | sense | acaggtaccgccaccatggagagtgacagctttgaagat | 55 |
| | antisense | gcgctcgagttagagagtagtggaagtgtg | 56 |
| rhesus | sense | ataggtaccgccaccatggagagtttcaattttgaagatctc | 57 |
| | antisense | gcgctcgagtcagagagtagtggaagtgtg | 58 |
| vervet | sense | ataggtaccgccaccatggagatttccaactttgaagatctc | 59 |
| | antisense | gcgctcgagtcagagagtactggaagtgtg | 60 |
| baboon | sense | ataggtaccgccaccatggagagtttcaattttgaagat | 61 |
| | antisense | gcgctcgagtcagagagtagtggaagtgtg | 62 |

Membrane Preparations

Membrane preparations for use in accordance with the methods of the present invention were generated as follows. 293E cell monolayers expressing CXCR2 receptors were washed twice with PBS and 5 ml of ice cold homogenizing buffer (for example, 10 mM HEPES pH 8.0, 10 mM EDTA). Cells were resuspended in membrane buffer and Dounce homogenized on ice 35 times. The membranes were collected by centrifugation at 15,000×g for 30 min. at 4° C. and resuspended in membrane storage buffer (10 mM Tris-HCl pH8.0, 1.2 mM MgSO$_4$, 0.1 mM EDTA, 25 mM NaCl, 1 unit/ml bacitracin) at a final concentration of approximately 5×10$^7$ cell equivalents per ml. Aliquots were flash frozen and stored at –80° C. Frozen aliquots were subsequently thawed, diluted, and sonicated on ice using a Branson Sonifier® 250 (4×5 sec, 40% output).

Prior to use in a binding assay, a membrane preparation is "calibrated" as described below to determine the amount of membrane preparation to be used. A frozen sample of a membrane preparation is thawed and the preparation diluted in assay buffer to obtain several different concentrations of membranes, for example, 1:5, 1:10, 1:20, 1:40 and so on. The diluted membrane preparation is sonicated in a bath style sonicator for 5 minutes at room temperature. Each dilution is plated in a 96-well plate, for example, with quintuplicate samples for binding of ligand and wells to evaluate non-specific binding in triplicate. The dilutions that yield approximately 200 cpm total counts are chosen for subsequent assays.

Binding Assays

For determining binding affinity for the orthologous CXCR2 receptors, described herein, the method of the present invention employs a binding assay such as the one described below. A suitable binding assay buffer for receptor binding consists of 10 mM Tris pH 8.0, 0.1 mM EDTA, 1.2 mM MgSO$_4$, 25 mM NaCl and 0.03% CHAPS (Sigma, St. Louis, Mo.). Competitor compounds, peptide or small molecule, were resuspended in 100% dimethyl sulfoxide (DMSO) and serially diluted prior to assay. Binding reactions were carried out in 96-well microtiter plates, 60 µl reaction volume per well in the presence of 0.1nM $^{125}$I-CXCR2 (NEN, Boston, Mass.). Binding reactions were shaken for 5 minutes subsequent to addition of labeled CXCR2 and prior to addition of membrane. Reaction mixtures were then incubated for 1 hour at room temperature with shaking. At the end of the incubation period, 50 µl of the reaction mixtures were transferred to glass fiber filterplates, for example, Multiscreen-FC, Opaque plates 1.2 uM type C filter (Millipore Corporation, Bedford, Mass.) which had been pre-blocked with 0.3% polyethyleneimine (PEI) (Sigma, St. Louis, Mo.), and washed 4 times with 100 µl/well of washing buffer. A suitable washing buffer is 10 mM Tris pH 8.0, 1mM MgSO$_4$, 0.5 mM EDTA, 25 mM NaCl, 0.03% CHAPS, and 0.5% BSA. 50 µl of scintillation fluid was added to each well and plates were counted in a Wallac Microbeta® TriLux for 1 min. per well.

As with the B$_1$ receptor, coding regions for the CXCR2 from 6 primate species were cloned and characterized in order to assess the species-specificity profiles of potential small molecule antagonist molecules. The relevant sequences were obtained, as described above, by performing PCR directly on genomic DNA obtained from each species. A pairwise comparison of percent amino acid identity among the CXCR2 receptor orthologues is shown in FIG. 17. Even though the difference among amino acids sequences of the orthologues is not extensive, single amino acid changes can significantly alter the binding affinity of small molecule ligands from one orthologue to the next.

For example, a single amino acid of the cholecystokinin-B receptor, at position 319 in the sixth transmembrane domain, is critical for high affinity binding of small drug-like molecules. This position is occupied by valine in the human receptor and leucine in the canine orthologue. Substitution of the valine in the human receptor with a leucine decreases binding affinity of L365260 by 20-fold. This result shows that interspecies differences at a single amino acid position can alter binding affinity when testing small drug-like molecules (Beinborn, M. et al. *Nature* Mar. 25, 1993; 362 (6418):348–350.)

Figure 14:
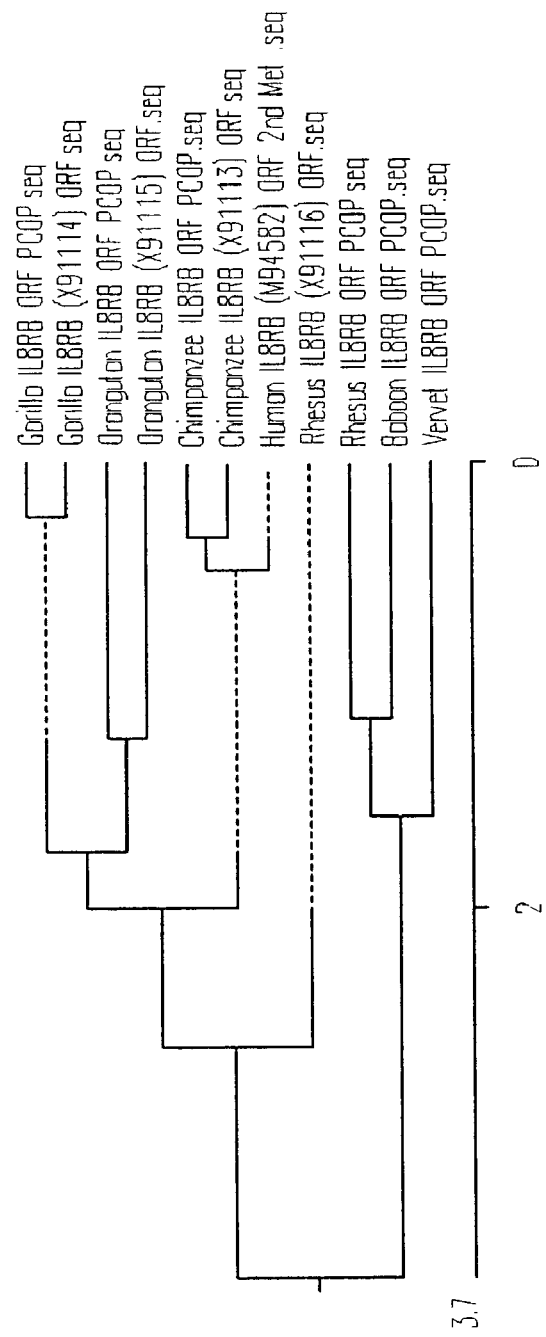
FIGS. 14 and 15 are schematics depicting putative phylogenetic relatedness of the CXCR2 receptor orthologues.
Figure 15:
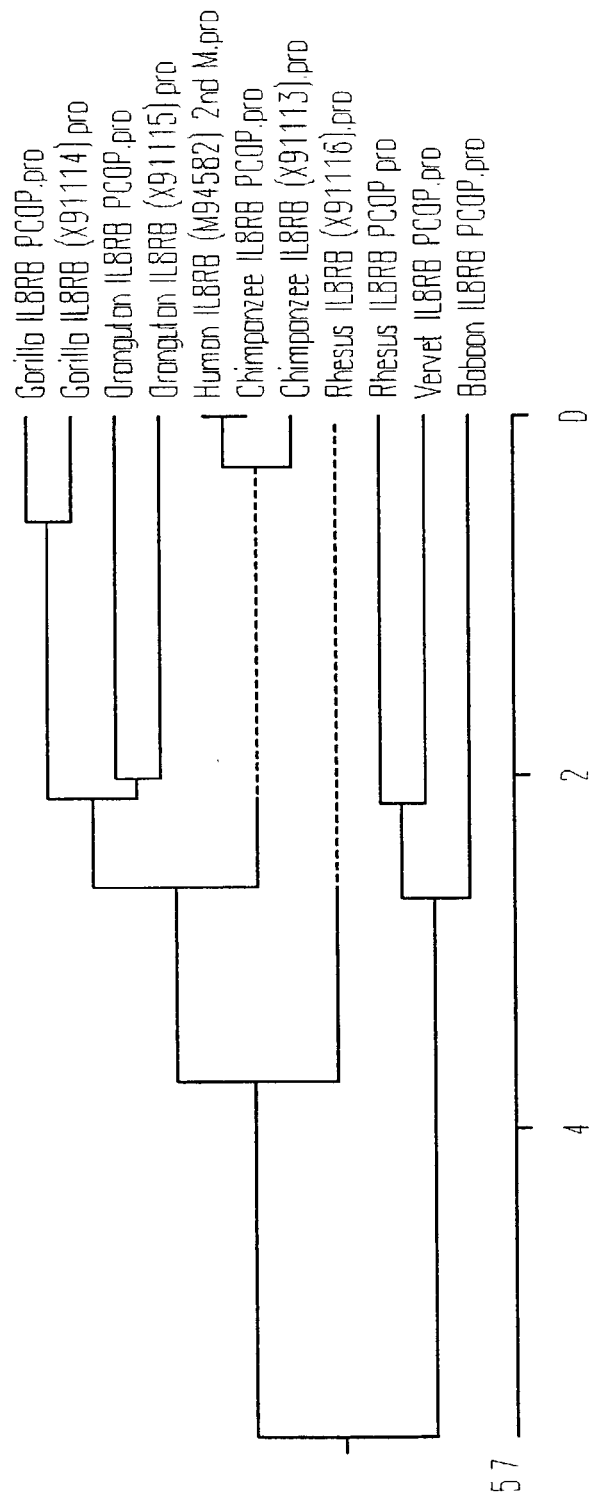
Figure 18:
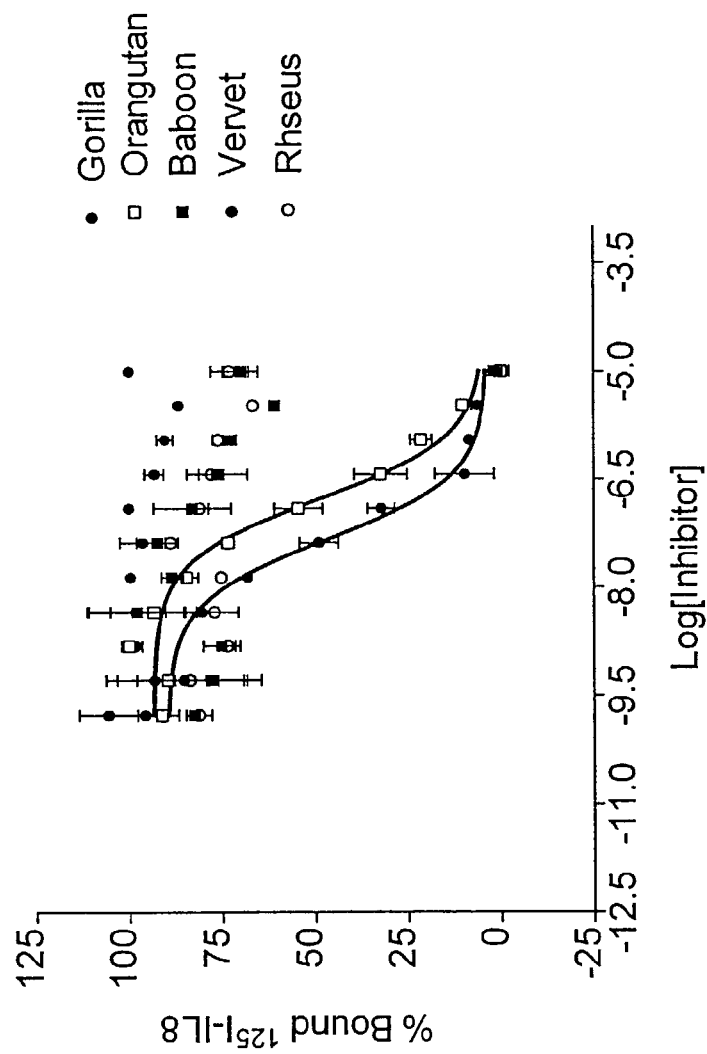
FIGS. 18 and 19 show the results of comparison of activity of selective (18) and non-selective (19) test compounds at non-human vs. human CXCR2 receptor orthologues.
Figure 19:
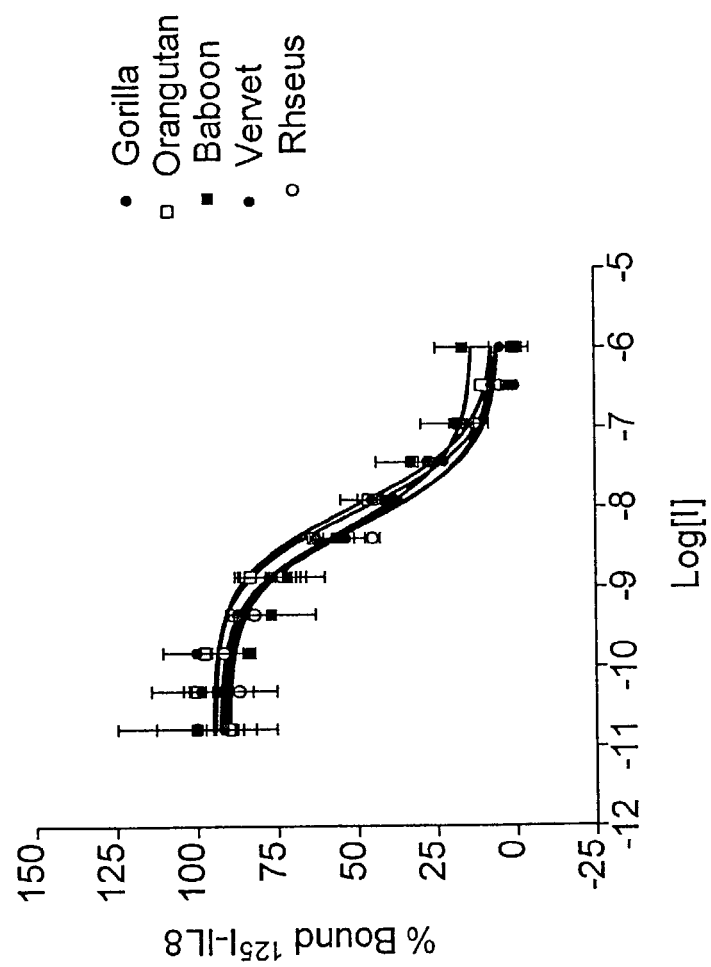

A dendritic chart showing a putative evolutionary relationship among the sequences (FIGS. 14 and 15) is consistent with current concepts and demonstrates that primates are very closely related to the human nucleotide sequence (93.4–99.4% identical).

The K$_d$ for $^{125}$CXCR2 for the human and monkey receptors is approximately 0.1 nM. The B$_{max}$ values for the monkey receptors varied from 0.5 to 2 pmols/mg of membrane protein.

What is claimed is:

1. A method of identifying a compound that modulates bradykinin $B_1$ receptor activity, comprising:
   (a) contacting a test compound with a bradykinin $B_1$ receptor comprising an amino acid sequence chosen from SEQ ID NO: 1, SEQ ID NO: 2, SEQ ID NO: 3, SEQ ID NO: 4, SEQ ID NO: 5 and SEQ ID NO: 6; and
   (b) measuring an effect of said compound on said receptor, wherein the effect to be measured is displacement of a ligand from the receptor, phosphatidyl inositol hydrolysis, release of intracellular Ca++, and arachidonic acid release.

2. The method of claim 1, wherein the effect to be measured is displacement of a ligand from the receptor and wherein the ligand is chosen from des-$Arg^{10}$-kallidin, des-$Arg^{10}Leu^9$-kallidin, des-$Arg^9$-bradykinin, des-$Arg^9Leu^8$-bradykinin.

3. The method of claim 1, wherein said bradykinin $B_1$ receptor is expressed by a recombinant host cell.

4. The method of claim 1, wherein said test compound is a peptidic ligand.

5. The method of claim 1, wherein said test compound is a non-peptidic ligand.

* * * * *

UNITED STATES PATENT AND TRADEMARK OFFICE
CERTIFICATE OF CORRECTION

| | |
|---|---|
| PATENT NO. | : 7,041,463 B2 |
| APPLICATION NO. | : 10/237563 |
| DATED | : May 9, 2006 |
| INVENTOR(S) | : Horlick et al. |

It is certified that error appears in the above-identified patent and that said Letters Patent is hereby corrected as shown below:

Title Page:

(75) Inventors:

Delete "Xiao Ge Chen, Princton, NJ (US)" and insert --Xiao Ge Chen, Princeton, NJ (US)--

Signed and Sealed this

Eighteenth Day of July, 2006

JON W. DUDAS
*Director of the United States Patent and Trademark Office*